United States Patent [19]
DeBacker et al.

[11] Patent Number: 6,013,481
[45] Date of Patent: Jan. 11, 2000

[54] ISOLATED, NUCLEIC ACID MOLECULES WHICH CODE FOR GAGE TUMOR REJECTION ANTIGEN, THE TUMOR REJECTION ANTIGEN, AND USES THEREOF

[75] Inventors: Olivier DeBacker; Benoit van den Eynde; Thierry Boon-Falleur, all of Brussels, Belgium

[73] Assignee: Ludwig Institute for Cancer Research, New York, N.Y.

[21] Appl. No.: 08/669,161

[22] Filed: Jun. 24, 1996

Related U.S. Application Data

[63] Continuation-in-part of application No. 08/531,662, Sep. 21, 1995, Pat. No. 5,858,689, which is a continuation-in-part of application No. 08/370,648, Jan. 10, 1995, Pat. No. 5,648,226, which is a continuation-in-part of application No. 08/250,162, May 27, 1994, Pat. No. 5,610,013, which is a continuation-in-part of application No. 08/096,039, Jul. 22, 1993, abandoned.

[51] Int. Cl.[7] .................................................. C12N 15/12
[52] U.S. Cl. .................. 435/69.3; 424/185.1; 424/277.1; 435/252.3; 435/320.1; 536/23.5
[58] Field of Search ........................ 536/23.5; 424/185.1, 424/277.1; 514/2; 435/6, 69.3, 320.1, 252.3

[56] References Cited

U.S. PATENT DOCUMENTS

| 5,610,013 | 3/1997 | Van Den Eynde et al. ................. 435/6 |
| 5,648,226 | 7/1997 | Van Den Eynde et al. ............ 435/7.24 |

FOREIGN PATENT DOCUMENTS

WO 95 03422  2/1995  WIPO .

OTHER PUBLICATIONS

Van den Eynde et al., "A New Family of Genes Coding For An Antigen Recognized By Autologous Cytolytic T Lymphocytes On A Human Melanoma", J. Exp. Med. 182: 689–698 (1995).

Herin et al., "Production of Stable Cytolytic T–Cell Clones Directed Against Autologous Human Melanoma", Int. J. Cancer 39: 390–396 (1987).

Wölfel et al., "Lysis of Human Melanoma Cells By Autologous Cytolytic T Cell Clones", J. Exp. Med. 170: 797–810 (Sep. 1989).

Van Den Eynde et al., "Presence On a Human Melanoma of Multiple Antigens Recognized by Autologous CTL", Int. J. Cancer 44: 634–640 (1989).

Van der Bruggen et al., "A Gene Encoding An Antigen Recognized By Cytolytic T Lymphocytes On a Human Melanoma", Science 254: 1643–1647 (Dec. 1991).

Brasseur et al., "Human Gene MAGE–1, which codes for a tumor rejection antigen, is expressed by some breast tumors", Int. J. Cancer 52: 839–841 (1992).

Traversari et al., "Transfection and expression of a gene coding for a human melanoma antigen recognized by autologous cytolytic T lymphocytes", Immunogenetics 35: 145–152 (1992).

Traversari et al., "A Nonapeptide Encoded by Human Gene MAGE–1 Is Recognized on HLA–A1 By Cytolytic T Lymphocytes Directed Against Tumor Antigen MZ2–E", J. Exp. Med. 176: 1453–1457 (Nov. 1992).

Wallace, B. et al. in Guide to Molecule Cloning Techniques, Meth. Enzymol. 152:432–443, 1987.

Sambrook, J. et al. (ed.), Molecular Cloning, 2nd edition, CSH Lab. Press, 1989, p. 11.47, 1989.

*Primary Examiner*—Thomas M. Cunningham
*Attorney, Agent, or Firm*—Fulbright & Jaworski, LLP.

[57] ABSTRACT

A new family of tumor rejection antigen precursors, and the nucleic acid molecules which code for them, are disclosed. These tumor rejection antigen precursors are referred to as GAGE tumor rejection antigen precursors, and the nucleic acid molecules which code for them are referred to as GAGE coding molecules. Various diagnostic and therapeutic uses of the coding sequences and the tumor rejection antigens, and their precursor molecules are described. Tumor rejection antigens are also shown.

14 Claims, 8 Drawing Sheets

```
                Antigenic
                Peptide
GAGE-1  MS-WRGRST-YRPRRYVEPPEMI GPMRPEQFSDEVEPATPEEGEPATQ RQDPAAAQEGEDEGASAGQGPKPEA   7
GAGE-2  MS-WRGRST-YRPRRYVEPPEMI GPMRPEQFSDEVEPATPEEGEPATQ RQDPAAAQEGEDEGASAGQGPKPEA   7
GAGE-3  MNLSRGKSTYVWPRRRYVQPPEMI GPMRPEQFSDEVEPATPEEGEPATQ RQDPAAAQEGEDEGASAGQGPKPEA   7
GAGE-4  MS-WRGRSTYVWPRRRYVQPPEMI GPMRPEQFSDEVEPATPEEGEPATQ RQDPAAAQEGEDEGASAGQGPKPEA   7
GAGE-5  MS-WRGRSTYVWPRRRYVQPPEVI GPMRPEQFSDEVEPATPEEGEPATQ RQDPAAAQEGEDEGASAGQGPKPEA   7
GAGE-6  MS-WRGRSTYVWPRRRYVQPPEVI GPMRPEQFSDEVEPATPEEGEPATQ RQDPAAAQEGEDEGASAGQGPKPEA   7

GAGE-1  DSQEQGHPQTGCECEDGPDGQEMDP PNPEEVKTPEEEMRSHYVAQTGILW LLMNNCFLMLSPRKP  13
GAGE-2  HSQEQGHPQTGCECEDGPDGQEMDP PNPEEVKTPEEGEKQSQC------- ---------------  11
GAGE-3  DSQEQGHPQTGCECEDGPDGQEMDP PNPEEVKTPEEGEKQSQC------- ---------------  11
GAGE-4  DSQEQGHPQTGCECEDGPDGQEMDP PNPEEVKTPEEGEKQSQC------- ---------------  11
GAGE-5  DSQEQGHPQTGCECEDGPDGQEMDP PNPEEVKTPEEGEKQSQC------- ---------------  11
GAGE-6  DSQEQGHPQTGCECEDGPDGQEVDP PNPEEVKTPEEGEKQSQC------- ---------------  11
```

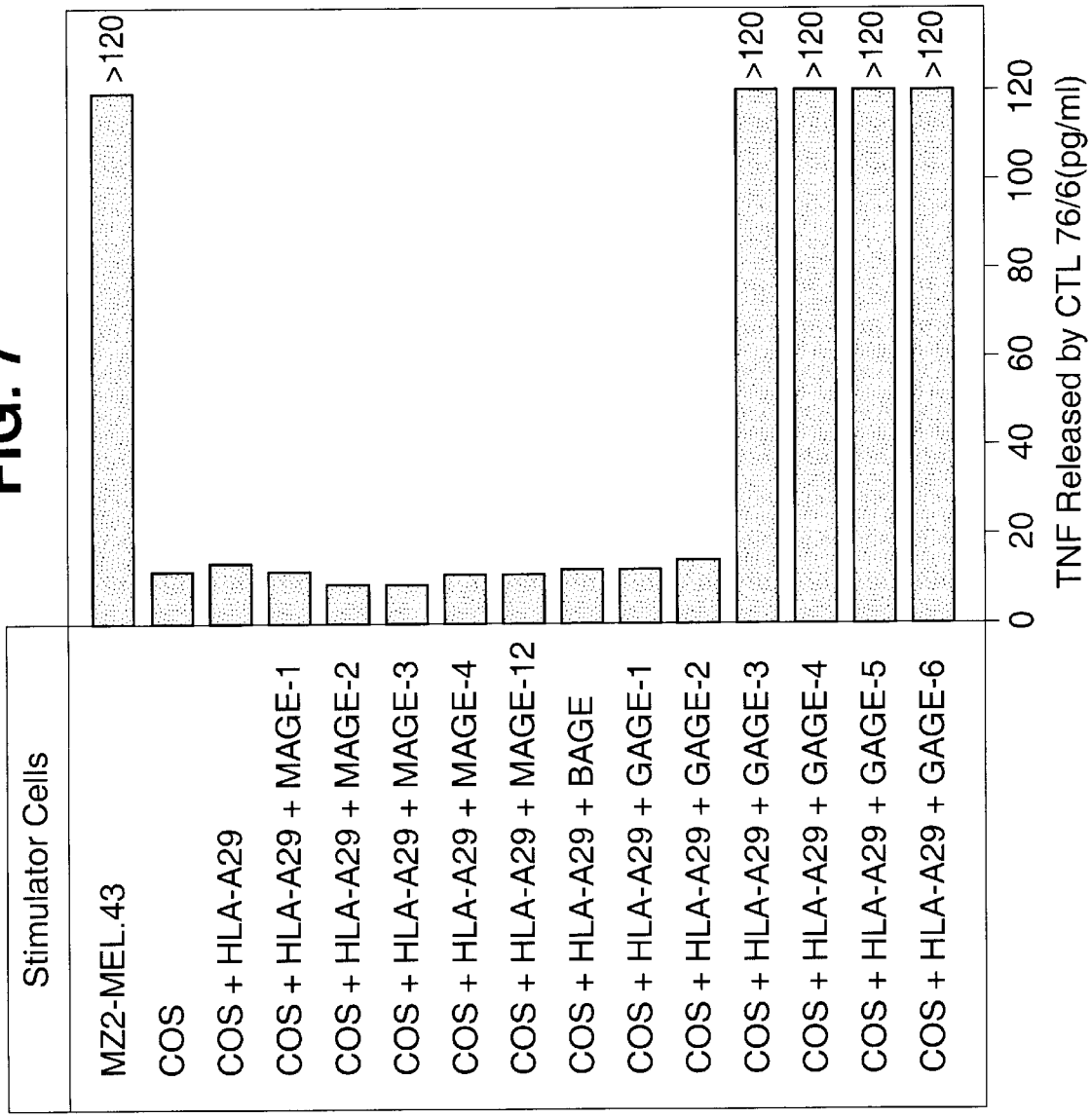

SEQUENCE LISTING (1) GENERAL INFORMATION:

(iii) NUMBER OF SEQUENCES: 29

(2) INFORMATION FOR SEQ ID NO: 1:

(i) SEQUENCE CHARACTERISTICS:
      (A) LENGTH: 646 base pairs
      (B) TYPE: nucleic acid
      (C) STRANDEDNESS: single
      (D) TOPOLOGY: linear (xi) SEQUENCE DESCRIPTION: SEQ ID NO:1:

```
CTGCCGTCCG GACTCTTTTT CCTCTACTGA GATTCATCTG TGTGAAATAT          50

GAGTTGGCGA GGAAGATCGA CCTATCGGCC TAGACCAAGA CGCTACGTAG         100

AGCCTCCTGA AATGATTGGG CCTATGCGGC CCGAGCAGTT CAGTGATGAA         150

GTGGAACCAG CAACACCTGA AGAAGGGGAA CCAGCAACTC AACGTCAGGA         200

TCCTGCAGCT GCTCAGGAGG GAGAGGATGA GGGAGCATCT GCAGGTCAAG         250

GGCCGAAGCC TGAAGCTGAT AGCCAGGAAC AGGGTCACCC ACAGACTGGG         300

TGTGAGTGTG AAGATGGTCC TGATGGGCAG GAGATGGACC CGCCAAATCC         350

AGAGGAGGTG AAAACGCCTG AAGAAGAGAT GAGGTCTCAC TATGTTGCCC         400

AGACTGGGAT TCTCTGGCTT TTAATGAACA ATTGCTTCTT AAATCTTTCC         450

CCACGGAAAC CTTGAGTGAC TGAAATATCA AATGGCGAGA GACCGTTTAG         500

TTCCTATCAT CTGTGGCATG TGAAGGGCAA TCACAGTGTT AAAAGAAGAC         550

ATGCTGAAAT GTTGCAGGCT GCTCCTATGT TGGAAAATTC TTCATTGAAG         600

TTCTCCCAAT AAAGCTTTAC AGCCTTCTGC AAAGAAAAAA AAAAAA           646
```

(2) INFORMATION FOR SEQ ID NO: 2:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (xi) SEQUENCE DESCRIPTION: SEQ ID NO: 2:

```
AGACGCTACG TAGAGCCT                                            18
```

(2) INFORMATION FOR SEQ ID NO: 3:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (xi) SEQUENCE DESCRIPTION: SEQ ID NO: 3:

```
CCATCAGGAC CATCTTCA                                            18
```

(2) INFORMATION FOR SEQ ID NO: 4:

(i) SEQUENCE CHARACTERISTICS:
      (A) LENGTH: 8 amino acids
      (B) TYPE: amino acid
      (D) TOPOLOGY: linear (xi) SEQUENCE DESCRIPTION: SEQ ID NO: 4:

```
Tyr Arg Pro Arg Pro Arg Arg Tyr
                 5

(2) INFORMATION FOR SEQ ID NO: 5:

(i) SEQUENCE CHARACTERISTICS:
         (A) LENGTH: 9 amino acids
         (B) TYPE:   amino acid
         (D) TOPOLOGY: linear (xi) SEQUENCE DESCRIPTION: SEQ ID NO: 5:

Thr Tyr Arg Pro Arg Pro Arg Arg Tyr
                 5

(2) INFORMATION FOR SEQ ID NO: 6:

(i) SEQUENCE CHARACTERISTICS:
         (A) LENGTH: 9 amino acids
         (B) TYPE:   amino acid
         (D) TOPOLOGY: linear (xi) SEQUENCE DESCRIPTION: SEQ ID NO: 6:

Tyr Arg Pro Arg Pro Arg Arg Tyr Val
                 5

(2) INFORMATION FOR SEQ ID NO: 7:

(i) SEQUENCE CHARACTERISTICS:
         (A) LENGTH: 10 amino acids
         (B) TYPE:   amino acid
         (D) TOPOLOGY: linear (xi) SEQUENCE DESCRIPTION: SEQ ID NO: 7:

Thr Tyr Arg Pro Arg Pro Arg Arg Tyr Val
                 5                   10

(2) INFORMATION FOR SEQ ID NO: 8:

(i) SEQUENCE CHARACTERISTICS:
         (A) LENGTH: 9 amino acids
         (B) TYPE:   amino acid
         (D) TOPOLOGY: linear (xi) SEQUENCE DESCRIPTION: SEQ ID NO: 8:

Arg Pro Arg Pro Arg Arg Tyr Val Glu
                 5

(2) INFORMATION FOR SEQ ID NO: 9:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (xi) SEQUENCE DESCRIPTION: SEQ ID NO: 9:

GACCAAGACG CTACGTAG                                                18

(2) INFORMATION FOR SEQ ID NO: 10:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (xi) SEQUENCE DESCRIPTION: SEQ ID NO: 10:

CCATCAGGAC CATCTTCA                                                18
```

(2) INFORMATION FOR SEQ ID NO: 11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 11:

```
GCGGCCCGAG CAGTTCA                                                   17
```

(2) INFORMATION FOR SEQ ID NO: 12:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 12:

```
Met Ser Trp Arg Gly Arg Ser Thr Tyr Arg Pro Arg Pro Arg Arg
              5                   10                  15
```

(2) INFORMATION FOR SEQ ID NO: 13:

(i) SEQUENCE CHARACTERISTICS:
        (A) LENGTH: 16 amino acids
        (B) TYPE: amino acid
        (D) TOPOLOGY: linear (xi) SEQUENCE DESCRIPTION: SEQ ID NO: 13:

```
Thr Tyr Arg Pro Arg Pro Arg Arg Tyr Val Glu Pro Pro Glu Met Ile
              5                   10                  15
```

(2) INFORMATION FOR SEQ ID NO: 14:

(i) SEQUENCE CHARACTERISTICS:
        (A) LENGTH: 538 base pairs
        (B) TYPE: nucleic acid
        (C) STRANDEDNESS: single
        (D) TOPOLOGY: linear (xi) SEQUENCE DESCRIPTION: SEQ ID NO: 14:

```
ACGCCAGGGA GCTGTGAGGC AGTGCTGTGT GGTTCCTGCC GTCCGGACTC               50
TTTTTCCTCT ACTGAGATTC ATCTGTGTGA AATATGAGTT GGCGAGGAAG              100
ATCGACCTAT CGGCCTAGAC CAAGACGCTA CGTAGAGCCT CCTGAAATGA              150
TTGGGCCTAT GCGGCCCGAG CAGTTCAGTG ATGAAGTGGA ACCAGCAACA              200
CCTGAAGAAG GGGAACCAGC AACTCAACGT CAGGATCCTG CAGCTGCTCA              250
GGAGGGAGAG GATGAGGGAG CATCTGCAGG TCAAGGGCCG AAGCCTGAAG              300
CTCATAGCCA GGAACAGGGT CACCCACAGA CTGGGTGTGA GTGTGAAGAT              350
GGTCCTGATG GGCAGGAGAT GGACCCGCCA AATCCAGAGG AGGTGAAAAC              400
GCCTGAAGAA GGTGAAAAGC AATCACAGTG TTAAAAGAAG ACACGTTGAA              450
ATGATGCAGG CTGCTCCTAT GTTGGAAATT TGTTCATTAA AATTCTCCCA              500
ATAAAGCTTT ACAGCCTTCT GCAAAGAAAA AAAAAAA                            538
```

(2) INFORMATION FOR SEQ ID NO: 15:

(i) SEQUENCE CHARACTERISTICS:
        (A) LENGTH: 560 base pairs
        (B) TYPE: nucleic acid
        (C) STRANDEDNESS: single (D) TOPOLOGY: linear (xi) SEQUENCE DESCRIPTION: SEQ ID NO: 15:

| | |
|---|---|
| CTCATATTTC ACACAGATGA GTTGGCGAGG AAGATCGACC TATTATTGGT | 50 |
| CTAGGCCAAT AATAGGTCGA TCTTCCTCGC CAACTCATAT TTCACACAGA | 100 |
| TGAATCTCAG TAGAGGAAAA TCGACCTATT ATTGGCCTAG ACCAAGGCGC | 150 |
| TATGTACAGC CTCCTGAAGT GATTGGGCCT ATGCGGCCCG AGCAGTTCAG | 200 |
| TGATGAAGTG GAACCAGCAA CACCTGAAGA AGGGGAACCA GCAACTCAAC | 250 |
| GTCAGGATCC TGCAGCTGCT CAGGAGGGAG AGGATGAGGG AGCATCTGCA | 300 |
| GGTCAAGGGC CGAAGCCTGA AGCTGATAGC CAGGAACAGG GTCACCCACA | 350 |
| GACTGGGTGT GAGTGTGAAG ATGGTCCTGA TGGGCAGGAG ATGGACCCGC | 400 |
| CAAATCCAGA GGAGGTGAAA ACGCCTGAAG AAGGTGAAAA GCAATCACAG | 450 |
| TGTTAAAAGA AGGCACGTTG AAATGATGCA GGCTGCTCCT ATGTTGGAAA | 500 |
| TTTGTTCATT AAAATTCTCC CAATAAAGCT TTACAGCCTT CTGCAAAGAA | 550 |
| AAAAAAAAAA | 560 |

(2) INFORMATION FOR SEQ ID NO: 16:

(i) SEQUENCE CHARACTERISTICS:
        (A) LENGTH: 540 base pairs
        (B) TYPE: nucleic acid
        (C) STRANDEDNESS: single
        (D) TOPOLOGY: linear (xi) SEQUENCE DESCRIPTION: SEQ ID NO: 16:

| | |
|---|---|
| CGCCAGGGAG CTGTGAGGCA GTGCTGTGTG GTTCCTGCCG TCCGGACTCT | 50 |
| TTTTCCTCTA CTGAGATTCA TCTGTGTGAA ATATGAGTTG GCGAGGAAGA | 100 |
| TCGACCTATT ATTGGCCTAG ACCAAGGCGC TATGTACAGC CTCCTGAAAT | 150 |
| GATTGGGCCT ATGCGGCCCG AGCAGTTCAG TGATGAAGTG GAACCAGCAA | 200 |
| CACCTGAAGA AGGGGAACCA GCAACTCAAC GTCAGGATCC TGCAGCTGCT | 250 |
| CAGGAGGGAG AGGATGAGGG AGCATCTGCA GGTCAAGGGC CGAAGCCTGA | 300 |
| AGCTGATAGC CAGGAACAGG GTCACCCACA GACTGGGTGT GAGTGTGAAG | 350 |
| ATGGTCCTGA TGGGCAGGAG ATGGACCCGC CAAATCCAGA GGAGGTGAAA | 400 |
| ACGCCTGAAG AAGGTGAAAA GCAATCACAG TGTTAAAAGA AGGCACGTTG | 450 |
| AAATGATGCA GGCTGCTCCT ATGTTGGAAA TTTGTTCATT AAAATTCTCC | 500 |
| CAATAAAGCT TTACAGCCTT CTGCAAAAAA AAAAAAAAA | 540 |

(2) INFORMATION FOR SEQ ID NO: 17:

(i) SEQUENCE CHARACTERISTICS:
        (A) LENGTH: 532 base pairs
        (B) TYPE: nucleic acid
        (C) STRANDEDNESS: single
        (D) TOPOLOGY: linear (xi) SEQUENCE DESCRIPTION: SEQ ID NO: 17:

| | |
|---|---|
| AGCTGTGAGG CAGTGCTGTG TGGTTCCTGC CGTCCGGACT CTTTTTCCTC | 50 |
| TACTGAGATT CATCTGTGTG AAATATGAGT TGGCGAGGAA GATCGACCTA | 100 |
| TTATTGGCCT AGACCAAGGC GCTATGTACA GCCTCCTGAA GTGATTGGGC | 150 |
| CTATGCGGCC CGAGCAGTTC AGTGATGAAG TGGAACCAGC AACACCTGAA | 200 |

```
GAAGGGGAAC CAGCAACTCA ACGTCAGGAT CCTGCAGCTG CTCAGGAGGG        250

AGAGGATGAG GGAGCATCTG CAGGTCAAGG GCCGAAGCCT GAAGCTGATA        300

GCCAGGAACA GGGTCACCCA CAGACTGGGT GTGAGTGTGA AGATGGTCCT        350

GATGGGCAGG AGATGGACCC GCCAAATCCA GAGGAGGTGA AAACGCCTGA        400

AGAAGGTGAA AAGCAATCAC AGTGTTAAAA GAAGGCACGT TGAAATGATG        450

CAGGCTGCTC CTATGTTGGA AATTTGTTCA TTAAAATTCT CCCAATAAAG        500

CTTTACAGCC TTCTGCAAAG AAAAAAAAAA AA                          532

(2) INFORMATION FOR SEQ ID NO: 18:

(i) SEQUENCE CHARACTERISTICS:
        (A) LENGTH: 539 base pairs
        (B) TYPE: nucleic acid
        (C) STRANDEDNESS: single
        (D) TOPOLOGY: linear (xi) SEQUENCE DESCRIPTION: SEQ ID NO: 18:

GCCAGGGAGC TGTGAGGCAG TGCTGTGTGG TTCCTGCCGT CCGGACTCTT         50

TTTCCTCTAC TGAGATTCAT CTGTGTGAAA TATGAGTTGG CGAGGAAGAT        100

CGACCTATTA TTGGCCTAGA CCAAGGCGCT ATGTACAGCC TCCTGAAGTG        150

ATTGGGCCTA TGCGGCCCGA GCAGTTCAGT GATGAAGTGG AACCAGCAAC        200

ACCTGAAGAA GGGGAACCAG CAACTCAACG TCAGGATCCT GCAGCTGCTC        250

AGGAGGGAGA GGATGAGGGA GCATCTGCAG GTCAAGGGCC GAAGCCTGAA        300

GCTGATAGCC AGGAACAGGG TCACCCACAG ACTGGGTGTG AGTGTGAAGA        350

TGGTCCTGAT GGGCAGGAGG TGGACCCGCC AAATCCAGAG GAGGTGAAAA        400

CGCCTGAAGA AGGTGAAAAG CAATCACAGT GTTAAAAGAA GACACGTTGA        450

AATGATGCAG GCTGCTCCTA TGTTGGAAAT TTGTTCATTA AAATTCTCCC        500

AATAAAGCTT TACAGCCTTC TGCAAAAAAA AAAAAAAA                    539

(2) INFORMATION FOR SEQ ID NO: 19:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 19:

ACTCCATGAG GTATTTC                                             17

(2) INFORMATION FOR SEQ ID NO: 20:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 20:

TTTCACCACA TCCGTGT                                             17

(2) INFORMATION FOR SEQ ID NO: 21:

(i) SEQUENCE CHARACTERISTICS:
        (A) LENGTH: 14 amino acids
        (B) TYPE:AMINO
        (B) TYPE:AMINO
```

```
          (D) TOPOLOGY: linear (xi) SEQUENCE DESCRIPTION: SEQ ID NO: 21:

Arg Ser Thr Tyr Tyr Trp Pro Arg Pro Arg Arg Tyr Val Gln
                 5                  10

(2) INFORMATION FOR SEQ ID NO: 22:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (xi) SEQUENCE DESCRIPTION: SEQ ID NO: 22:

ACTCCATGAG GTATTTC                                                      17

(2) INFORMATION FOR SEQ ID NO: 23:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (xi) SEQUENCE DESCRIPTION: SEQ ID NO: 23:

TTTCACCACA TGCGTGT                                                      17

(2) INFORMATION FOR SEQ ID NO: 24:

(i) SEQUENCE CHARACTERISTICS:
          (A) LENGTH: 14 amino acids
          (B) TYPE: amino acid
          (D) TOPOLOGY: linear (xi) SEQUENCE DESCRIPTION: SEQ ID NO: 24:

Arg Ser Thr Tyr Tyr Trp Pro Arg Pro Arg Arg Tyr Val Gln
                 5                  10

(2) INFORMATION FOR SEQ ID NO: 25:

(i) SEQUENCE CHARACTERISTICS:
          (A) LENGTH: 9 amino acids
          (B) TYPE: amino acid
          (D) TOPOLOGY: linear (xi) SEQUENCE DESCRIPTION: SEQ ID NO: 25:

Tyr Tyr Trp Pro Arg Pro Arg Arg Tyr
                 5

(2) INFORMATION FOR SEQ ID NO: 26:

(i) SEQUENCE CHARACTERISTICS:
          (A) LENGTH: 9 amino acids
          (B) TYPE: amino acid
          (D) TOPOLOGY: linear (ix) FEATURE:
          (D) OTHER INFORMATION:   Each Xaa may be any amino acid (xi) SEQUENCE DESCRIPTION: SEQ ID NO: 26:

Xaa Xaa Trp Xaa Xaa Xaa Xaa Xaa Tyr
                 5

(2) INFORMATION FOR SEQ ID NO: 27:

(i) SEQUENCE CHARACTERISTICS:
          (A) LENGTH: 9  amino acids
```

(B) TYPE: amino acid
        (D) TOPOLOGY: linear (xi) SEQUENCE DESCRIPTION: SEQ ID NO: 27:

Tyr Trp Pro Arg Pro Arg Arg Tyr Val
                5

(2) INFORMATION FOR SEQ ID NO: 28:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO: 28:

Tyr Tyr Trp Pro Arg Pro Arg Arg Tyr Val
                5                   10

(2) INFORMATION FOR SEQ ID NO: 29:

(i) SEQUENCE CHARACTERISTICS:
        (A) LENGTH: 11461 base pairs
        (B) TYPE: nucleic acid
        (C) STRANDEDNESS: double
        (D) TOPOLOGY: linear (xi) SEQUENCE DESCRIPTION: SEQ ID NO: 29:

| | | | | |
|---|---|---|---|---|
| GAGCTCGCTG | CAGCCTTGAC | CTCCTGGGCT | CAAGCGCTCC | TCCCACCTCA | 50 |
| GCCTCCTGAG | TAGCTGTGAG | TATAGGTACA | TGCCACCATG | CNCAGCTAAT | 100 |
| TTTTCGATGG | TTTTTTTGTT | TGTTTTTTGT | AGTGATGAGA | TTTTCTGATG | 150 |
| TTGCTTAGGC | TGGTCTCGAA | GTCCTGAGCT | CAGGTGATCT | GGCCAGCTCA | 200 |
| GCCTCCCAAA | ATACTAGGAT | TACAGGCGTG | ANTTGGCCTG | GTCTGGTTTT | 250 |
| TCTTATATAG | GGGTCTTATC | TATATAAAGA | CTAAAGTTAA | TCTGTGCCTT | 300 |
| TGTGCGGGTG | GGCTAAGAGC | ATGATGACTT | TTATCATTCT | ATTGATTTAA | 350 |
| AGAAAACTGT | CCTTGACTTA | CCAGTGTGTA | AGTCCATGAA | AGCATAATTC | 400 |
| TGTTGAAAGC | ATATATTGTT | AATGGGTGTT | GGGAACCGTG | CACTTTCCGC | 450 |
| TGCTGTGGGA | GCATGTCCTT | GGAGGTACCT | TTCATCTGTT | TTCTCAACTC | 500 |
| CAAACATCTT | AGGACCATGG | GTTGTGACTG | GTAGGACTAT | GTATCTTGCT | 550 |
| GCTTTCAAGA | CGGAGTATAT | TTTCACGTGG | TGTCACTCTG | GCTGTCCTGT | 600 |
| TTCCCTAATA | CTGTCACTTC | ACCCTCTGCG | ATTCTGATGC | TACAAATGAT | 650 |
| AGATATCGTT | TTAGCATTTT | CTTACGGGTC | CTAGCGATTC | TATTCATTTT | 700 |
| TCTTTCAGTC | TCTTTCTCTG | ACTTGTTCAC | ATTGAACAAT | TTCCTTTTGG | 750 |
| GATAGGTTGC | TATTTCTGTT | TTCGCAGGTG | GTTTACCTGT | CTTCCCAGCC | 800 |
| AGTCACAGTG | GTCCTTGTCC | CCATGGTGGG | TCCGGGGCAA | GAGAGGGCCC | 850 |
| TGGGTTGGGG | GTGGGGTTCA | GTTGAAGATG | GGGTGAGTTT | TGAGGGGAGC | 900 |
| ACTACTTGAG | TCCCAGAGGC | ATAGGAAACA | GCAGAGGGAG | GTGGGATTCC | 950 |
| CTTATCCTCA | ATGAGGATGG | GCATGGAGGG | TTTGGGGCGT | GGCGCTGGGA | 1000 |
| ACGGCAGCCC | TCCCCAGCCC | ACAGCCGCGC | ATGCTCCCTG | NTCCCGCCTC | 1050 |
| AGTGCGCATG | TTCACTGGGC | GTCTTCTGCC | CGGCCCCTTC | GCCCACGTGA | 1100 |
| AGAACGCCAG | GGAGCTGTGA | GGCAGTGCTG | TGTGGTTCCT | GCCGTCCGGA | 1150 |
| CTCTTTTTCC | TCTACTGAGA | TTCATCTGGT | AGGTGTGCAG | GCCAGTCATC | 1200 |

-continued

| | |
|---|---|
| CCGGGGGCTG AAGTGTGAGT GAGGGTGGAG AGGGCCTCGG GTGGGTCAGG | 1250 |
| CGGGTCCGTT CCTGGTCTGT GGCCTCCGAG GGAGAAGGGC CACGAGGTTA | 1300 |
| CGTACCTCCT TACCCTTCAC AGGCTGCGAG GCCACCGGCG GCTTCGTGGT | 1350 |
| CGTGAAGGGG CCTGGACGGG GAGGAAGGTG GGCCGTGGAG GGGAGGCTGT | 1400 |
| CAGGGGCTCA GGTGAAGACG GGGTGAGTGC TGTTGGGGGG ATGGAAGTCC | 1450 |
| CGAGGTGCCG GGATCCCCGA CGACACAGGG CAGATTCCCT GAATGGGCCC | 1500 |
| GGCGGGGGCG AGGCGGGCGG TGAAGAAGGG GCCTGGCACC TGGGAAGGCT | 1550 |
| GCGGCCTGGC GAGCGCCCCC CCCAGCGGTG TGGAGTGCGG AGCGCCCGAG | 1600 |
| TGAGAAGCAC TGCAAGGTCT CACCTCCGCC ATGGAAGGTC CGAAAACAGT | 1650 |
| GGGAAGGAGT GGGCGAGGCA GTGCGGTCCA ACCAAACTTG TTGTGAGGGG | 1700 |
| GGGTGAATGG CTCTAGGAAG TGGGAGTGTG CCCAAAGCAG CAATCACGAG | 1750 |
| AATTGTGATT CACTAGGGTT TTCGTGGGGA GTGCACTTGT GAAACTAAAC | 1800 |
| CTCATCAGAA ATGACCTCTG TCTGCGGGGC GCAGTGGCGC TCGCCTACGT | 1850 |
| AGTCCCAGTT ACTGGGACA CTGAGGTGGG AGGATCCCTT GAGCGGGAGG | 1900 |
| TCGAGGCTGC AGTGAGCTGT GATCACGCCG CTGCACTCCA GCCTGAGCAA | 1950 |
| CACAGCGATA CCGCGTGTCC AAAAGAAATT TAGAAAAAAA TGTCCTCTGC | 2000 |
| CTTTTGCCAC ACGCCTTAAG ATGATTGCTC TGCCAGCCTG GCCAGCAGAA | 2050 |
| GTGGCTTTGT AGGCACTCAG ACAGCGTACA CACGTATGCT TAACTCTGGG | 2100 |
| ACTTATTTTG AGAGTATTTT CAAAAGTAAA ACGGCAAGTT AACATTTATC | 2150 |
| CATGGAAGTG ATCGAATATA GCAGCCCTGT GGAGCGCACG TTCCCAATCA | 2200 |
| CGGTTGTCTG TTTTCAGTGT GAAATATGAG TTGGCGAGGA AGATCGACCT | 2250 |
| ATTATTGGCC TAGACCAAGG CGCTATGTAC AGCCTCCTGA AATGATTGGG | 2300 |
| CCTATGCGGG TGAGTGCTTA AACGTTAATT CGATGTTTTC TATTAGTAGA | 2350 |
| AATTAATTTT TGTGATAGCG TCGTTGCATT AGTGTGGAAA TGCTGATAAA | 2400 |
| GGTCTTTCCT GCTCATAAAA AATGAGGATG GCATCTCATG AAGGAAACAT | 2450 |
| TGATTCTGGA GGATTTTTTT TTTTCCTCTC GTGTTCTTCA GCTTTTGCCC | 2500 |
| ATGACTTCTT TCTCCGGCTT TGTTTGTTAA TGACAGATTG TACACATGTA | 2550 |
| TTCCAACACA GAGTATAATA GCCCCCAAAG TCCTCGTGCG TCACTTTTCT | 2600 |
| CACAGTAACC TCCCTGTGGG TGGAGTAACC TTATTGGGCA TAGAGCATAG | 2650 |
| AGTTGGAGAA ATGTCTTTAG GCTTAGTTAG GACCAGAAAT AGCTATGTAT | 2700 |
| TCTGTGTATA TATGTAAAAT TTTGTATCAA TAACGAAACT TATTTTTTAT | 2750 |
| TTGCACACCC ACACGTATTC CCCAGCCCGA GCAGTTCAGT GATGAAGTGG | 2800 |
| AACCAGCAAC ACCTGAAGAA GGGGAACCAG CAACTCAACG TCAGGATCCT | 2850 |
| GCAGCTGCTC AGGAGGGAGA GGATGAGGGA GCATCTGCAG GTCAAGGTGA | 2900 |
| GGGAAAGGGA AGAAGAACGT CTGCTGGTGT GTGCGTGTGT GTGTGTTCGT | 2950 |
| GTGTGTGTGT GCACGTGTGT GTGTGTTAGG CATTGTCACA TAGGAGGAAG | 3000 |
| AGGAGGAAAG AAAACAATGG AAAGAATGCC TGAAATTGAC TGGAAAAGCG | 3050 |
| AGGAGGCTAT GTAGTTTGCA GCTTAGCTTA GGCAAATCCC TCACTATGAT | 3100 |
| AAAAGTTCTC GACTTTATGA ATGAGAGAAT GGAGGTGCCA GGATTGTGTG | 3150 |
| TTATCCAAGA ACCCTTGACT GGTGAATACA ACATTTGTAC TGTGTTCTAA | 3200 |

| | |
|---|---|
| GGTTTGTGTC TTCCTATCAT GTATGTTGCT GGAAAGAAGG AAGTGATTTT | 3250 |
| GCTGAAAATG CTTAAAACTC AAAAGGCTTT ACTGTAAGGT AGCTTAGTAC | 3300 |
| TGACCCAAGA ATAGACCCAG TTCAGAGGAG CAGGAGCAGC TCCAAAAACC | 3350 |
| GAGTCGCTGA ATGTTGGCCC CCGTTTCCTT TGATTGATAT TTTTATATGG | 3400 |
| TACGTTTGAT AAAAGCTGGA TAAATGAGGA TACTGCCATA CAGGTAGCTG | 3450 |
| GTTTAGTGAT TTTTCTCAGC GGCCTTTAGG AGGTGATTAA ATCCTTTTAT | 3500 |
| GGTTAGAAAA GCAAAAACGG AATTATCCTG AGATTAACGT GAGATGGAAA | 3550 |
| TAATTTCTCC GAGATAAAAT GTTTTGAAAG GAAGCATTTA TGTAACGGAG | 3600 |
| GTCATGGATT ATTCCAGGGA TGCACTGTTA AAAGTTCCTA GAATCTGACT | 3650 |
| GACAACAATG CCCATTAATT GCTGTCCGCC CACTCCCTTA TTCTCAGTGC | 3700 |
| GGGGACAGTA TATTTTCTGT GATTCACAAA CAATGTTATA TTTGGTGCTT | 3750 |
| TGTTCTTCAC GGGGTTCATT TATGGAATAT TACCTTTAGG ACCTTCGGAC | 3800 |
| CTAAATATAA CTTTATTTGA ACAAAGTGAA GTTTCTCTTT ACCCCGATAG | 3850 |
| GTAATGGGTG TCGTGACTGT AAGATTTCCA TAGTCCTCAA ATCCATCCAG | 3900 |
| CTAATCAATC CTTCAGAAAC TGACATTGTA ATTGTAACTG AAATCCTACC | 3950 |
| CACGTGGTAG ACTTCAGATT TCTCACGTGA CGCACACTGC TGTTGGTACT | 4000 |
| CTAAGGCTGA ATATAAGCAT TATACATGTC CTGTGGTTTA TCCTTAGATT | 4050 |
| GTCATTTAGG AGAAAGGTCT AAAGCTGGGC TGAATGCCAT GCACTCATAG | 4100 |
| TCCCAGCTAC TTGGGAGGCC GAGGTGAGAG GATTGCTTGA GTCCTGGAGT | 4150 |
| TCAAGCCCAG CCTGGGAAAC ACAGTGAGAC CTCATTGCTA ATAAATAAAT | 4200 |
| AAATGAATAA ATAAATAAAC ACATAAATAA ATTCATTAAA TAAATAAAGT | 4250 |
| TTTCATGGTA TAGGAAAACA CAGATGCAAA GTTTTTGTGC CTAGTGGCTG | 4300 |
| GTAATGTTGC AAACGTAACT CCTTAGTGAA CTGTACCACT TAAAAATAGT | 4350 |
| TAAGATGGTA AATTTTAGGA TATCTGTATT TTTTACCACA ATTGGAAATT | 4400 |
| CCTTTCTTCC TAAAGTTCAG TGCAGTTATC ATATATTCTT TTAAATTTTT | 4450 |
| ACTGTATGTA TCTTCAAGAC ATAACATTCA TAGAAAATTT GCAAGAATAG | 4500 |
| TACAATGAAC TCATATACTG TTCATCTGGA TTCACCAATG TTAGTAGTTT | 4550 |
| CGCTTCATAG GTTTCACATC TCTTCCCTCC GTCTCTTACC GTGCTGCCCA | 4600 |
| CACACTACAC ACACACACTC ACACACACAT ACGGATATAT GTTTACTGTT | 4650 |
| ATTAATGCTG AATTGTCTCG ATAAAGTTTA GGGATTATGG TCCTTTACCC | 4700 |
| TATGTACTTG AGGGTGTGTA TATCGTCAGA ACAAAGAGAA AGTCATTTCT | 4750 |
| TGGATCCTCG AGCTCGAGGA TCCTGCAGCT GCTCAGGAGG GAGAGGATGA | 4800 |
| GGGAGCATCT GCAGGTCAAG GTGAGGGAAA GGGAAGAAGA ACGTCTGCTG | 4850 |
| GTGTGTGCGT GTGTGTGTGT TCGTGTGTGT GTGTGCACGT GTGTGTGTGT | 4900 |
| TAGGCATTGT CACATAGGAG GAAGAGGAGG AAAGAAAACA ATGGAAAGAA | 4950 |
| TGCCTGAAAT TGACTGGAAA AGCGAGGAGG CTATGTAGTT TGCAGCTTAG | 5000 |
| CTTAGGCAAA TCCCTCACTA TGATAAAAGT TCTCGACTTT ATGAATGAGA | 5050 |
| GAATGGAGGT GCCAGGATTG TGTGTTATCC AAGAACCCTT GACTGGTGAA | 5100 |
| TACAACATTT GTACTGTGTT CTAAGGTTTG TGTCTTCCTA TCATGTATGT | 5150 |
| TGCTGGAAAG AAGGAAGTGA TTTTGCTGAA AATGCTTAAA ACTCAAAAGG | 5200 |

| | |
|---|---|
| CTTTACTGTA AGGTAGCTTA GTACTGACCC AAGAATAGAC CCAGTTCAGA | 5250 |
| GGAGCAGGAG CAGCTCCAAA NACCGAGTCG CTGAATGTTG GCCCCCGTTT | 5300 |
| CCTTTGATTG ATATTTTTAT ATGGTACGTT TGATAAAAGC TGGATAAATG | 5350 |
| AGGATACTGC CATACAGGTA GCTGGTTTAG TGATTTTTCT CAGCGGCCTT | 5400 |
| TAGGAGGTGA TTAAATCCTT TTATGGTTAG AAAAGCAAAA ACGGAATTAT | 5450 |
| CCTGAGATTA ACGTGAGATG GAAATAATTT CTCCGAGATA AAATGTTTTG | 5500 |
| AAAGGAAGCA TTTATGTAAC GGAGGTCATG GATTATTCCA GGGATGCACT | 5550 |
| GTTAAAAGTT CCTAGAATCT GACTGACAAC AATGCCCATT AATTGCTGTC | 5600 |
| CGCCCACTCC CTTATTCTCA GTGCGGGGGA CAGTATATTT TCTGTGATTC | 5650 |
| ACAAACAATG TTATATTTGG TGCTTTGTTG CTTCACGGGG TTCATTTATG | 5700 |
| GAATATTACC TTTAGGACCT TCGGACCTAA ATATAACTTT ATTTGAACAA | 5750 |
| AGTGGAAGTT CTCTTTTACC CCGATAGGTA ATGGGTGTCG TGACTGTAAG | 5800 |
| ATTTCCATAG TCCTCAAATC CATCCAGCTA ATCAATCCTT CAGACCCTGA | 5850 |
| CATTGTAATT GTAACTGAAA TCCTACCCAC GTGGTAGACT TCAGATTTCT | 5900 |
| CAGCTGACAC ACACTGCTGT TGGTACTCTA GGGCTGAATA TAAGCATTAT | 5950 |
| ACATGTCCTG TGGTTTATCC TTAGATTGTC ATTTAGGAGA AAGGTCTAAA | 6000 |
| GCTGGGCTGA ATGCCATGCA CTCATAGTCC CAGCTACTTG GGAGGCCGAG | 6050 |
| GTGAGAGGAT TGCTTGAGTC CTGGAGTTCA AAGCCCAGCC TGGGAAACAC | 6100 |
| AGTGAGACCT CATTGCTAAT AAATAAATAA ATGAATAAAT AAATAAACAC | 6150 |
| ATAAATAAAT TCATTAAATA AATAAAGTTT TCATGGTATA GGAAAACACA | 6200 |
| GATGCAAAGT TTTTGTGCCT AGTGGCTGGT AATGTTGCAA ACGTAACTCC | 6250 |
| TTAGTGAACT GTACCACTTN NNNNTAGTTA AGATGGTAAA TTTTAGGATA | 6300 |
| TCTGTATTTT TTACCACAAT TGGAAATTCC TTTCTTCCTA AAGTTCAGTG | 6350 |
| CAGTTATCAT ATATTCTTTT AAATTTTTAC TGTATGTATC TTCAAGACAT | 6400 |
| AACATTCATA GAAAATTTGC AAGAATAGTA CAATGAACTC ATATACTGTT | 6450 |
| CATCTGGATT CACCAATGTG GTTAGTAGCT TTCGCTTCAT AGGTTTCACA | 6500 |
| TCTTCTTCCC TCCGTCTCTT ACCGTGCTGC CCACACACTC ACACACACAC | 6550 |
| ACTCACACAC ACATACGGAT ATATGTTTAC TGTTATTAAT GTGAATTGTC | 6600 |
| TCGATAAAGT TTCAGGGATT ATGGTCCTTT ACCCTATGTA CTTGAGGGTG | 6650 |
| TGTATATCGT CAGAACAAAG AGAAAGTCAT TTCTTGGATC ATCACTGCAC | 6700 |
| AAAGATAAAA ATCAGGAAAT TTAACAATGA GAAAATGGAG TCATTTAATC | 6750 |
| ACAGAGTGCA TACTCAAATT TTGCCAGCTT CCCCAGAAAT TTCTTTTTTC | 6800 |
| CTTTTTTTTT TCTTTGTTCG AGACGGAGTC TCTCTCTGTG GGCCAGGTTG | 6850 |
| GAGGGCAGTA GTGCGATCTC GGCTCACTGC AACCTACACC TCCCAGGTTC | 6900 |
| TAGGGATTCT CATGCCTCAG CCTCCCGTGT AGCTGGGACT ACAGGCGCCG | 6950 |
| GCCACTGCGG TCTTGAACTT CTGGCCTCAC CTGCTCTGCC CACCTTGGCA | 7000 |
| TCCCAAAATG TTTGGATTGC AGGCGTGAGA CCCCACGCCC GGCCCAGATA | 7050 |
| ATTTTATTGA TAGGATTTCT TTTTCTGATC CAGAGTCCAG TTGAGAATCA | 7100 |
| CACCTTGCAT GTGCTTTTCA GGTGTTTTTA GTTTCCTTTA ACCTGTAATG | 7150 |
| TTTCCTTAAT TTTTCTTGTC ATTCACGATA CGGACATTTT TGGAGAGGAT | 7200 |

| | |
|---|---|
| AGACCAGTTG GTTTGCAGAA TATTCTGTAG TTTGGGCTTT TTCATGTATT | 7250 |
| TTAAAAGAGT TTTCTCACTC AGCGTTTATT GGTGGCTACT CATGCCATGT | 7300 |
| AAGAGTCTAA GCGCTAGGAG TGTAAGTGCT GTGAGAGACG GGATTTGAGC | 7350 |
| CTTGAGTCAT TTAATACGAG AAGGACAATC AGAAGTAGAA TAAGAGAGAA | 7400 |
| GTGCAAAGGA GGCAGCAAAG TTGTCTGAGG GCAGTCTTCG GAAAGGAGGA | 7450 |
| GGGTNATATT TGGAACACCT TGTTTTCCTG TTTTCTGCTA ACGGACTCCT | 7500 |
| GAAATAATGT TCCTGGGATT CTTATCAACA CATTTATTAT TACGTTAGCT | 7550 |
| AAAGCTTTTA TATAATAATA CCGAGAGCAT GAATATCATT TTCTTATTCA | 7600 |
| TATTTTATGT TTTACTGCTT AAATTGATAC GTATTTTTTA TTTTTAAGGG | 7650 |
| CCGAAGCCTG AAGCTCATAG CCAGGAACAG GGTCACCCAC AGACTGGGTG | 7700 |
| TGAGTGTGAA GATGGTCCTG ATGGGCAGGA GATGGACCCG CCAAATCCAG | 7750 |
| AGGAGGTGAA AACGCCTGAA GAAGGTAGGC AATCCATTAG GCATGCACAT | 7800 |
| TGTAGGGTGT CTGTTTCCAC AGTATCATAT TGTAACTCTT ACTATGTTTT | 7850 |
| TGAGACGGAG TCTCGCTCTG AAGACCAGGC TGGAGTGCAG TGGTGCCATC | 7900 |
| TCGGCTCACT GGAAATTCTG TCTCCAGGGT TCAAGTGATT CTCCTGCCTG | 7950 |
| AGCCTCTGGC GGAGCCGGGC TTACAGGCAT GCTCCGCCGC GCCCAGCTAA | 8000 |
| TTGTTGTATT TTTAGTAGAG ACAGGGTTTC GTTATGTTGC ACAGGTTGTT | 8050 |
| CCCGAACTCC TGACCTCAGG TGATCCACCT GCCTCGACCA TTGAAATTGC | 8100 |
| CGGGATTACA GGCAGAGCCA CCGTGCCCGA CCCAGCATTA TATTTTTAAT | 8150 |
| AACAGAGAGG TAACAATACT GCGTCTTTAG TAACAGAGTT CTTATATAAA | 8200 |
| GGTTATTTGA AACGTAGTTC AGGCCCCAGC ACCCGGCTGA TAGACTGTCA | 8250 |
| GATAGGGAAA CAAAGTGAGT CAAAGCTATG TTGAATTAAA AGTTTTGAGT | 8300 |
| ATAAATCCTT AAACCAGTAG CTCACAATTT TCAGATGCTT TTGTAAAGGT | 8350 |
| CTGCTTTTAA TCAATACATA ACACGTTTGT AACACCCATC ACTTGGTGTG | 8400 |
| AAAAATGCTG AAGCACTCAT GCGGGTTCTA ATACCAGCTC TTACAGCCTT | 8450 |
| GGCGAGATTC TGAGTGAGTC CTTTCCCTTC TAAACCTATC TTTGGTTCTT | 8500 |
| ATGAAAATAG TGAGTTTAAG TCAGAGACTT TAAAACCATT TTGCATTCCG | 8550 |
| TTTCTTTCAT ACTCTGATCC TGTTGCATAG AATGCGTGGG ACACAGAGAT | 8600 |
| CATCTCTTCG CATGGTTTGT TAATCACAAA TCATGAAACC CTGGCCCGAG | 8650 |
| TCATCTGAAA ATCTCTGAAT TGAGATTTCA TTGTCAGTAA GACAGTGAGC | 8700 |
| GGGCCCTCTG CTTCATCCTA GTTTTTCCGT GTGGAGAGCT GAATACGTAG | 8750 |
| TATAAGATCT TGTGAAATTG TGAATTCTCC CTCTTCTTGG TTTGTTTGTT | 8800 |
| TGTTTGCGAC AGAGTCTCAG TGTGTCACCC AGGCTGGAGT GCAGTGATGC | 8850 |
| AATTTCAGCT CACTGCAACT TCTGGCTCCC AGCTAAAGCC GTCCTCCCAC | 8900 |
| CTCAGCCTCC CGAGTGGCTG GAACTACATG CACAAGCCAC CGTGCCTGAC | 8950 |
| TACATTTTTT TGTTTTCATT TTTGTAGAGA TGAGGTCTCA CTGTGTTGCC | 9000 |
| CAGGCAGGGT TTCTCTGGCT TTTAATGAAC AATTGCTTCT TTTTTTTCCT | 9050 |
| TTTATTTATT TATTATACTT TAAGTTTTAG GGTACATGTG ACGTTGTGCA | 9100 |
| GGTTAGTTAC ATACGTATAC ATGTGCCATG CTGTGCGCTG CACCCACTA | 9149 |
| CTCATCATCT AGCATTAGGT ACATCTCCCA GTGCTATCCC TCCCCCCTCC | 9199 |

-continued

| | |
|---|---|
| CCCCACCCGA CAACAGTCCC CAGGGTGTGA TATTCCCCTT CCTCTGTCCA | 9249 |
| TGTGATCTCA TTGTTCAGTT CCCACCTATG AGTGAGAATA TGCGGTGTTT | 9299 |
| GGTTTTTTGT TCTTGCGATA GTTTACTGAG AATGATGATT TCNAGTTTCA | 9349 |
| TCCATGTCCC TACAAAGGAC ATGAACTCTT CATTTTTTAG GGCTGCATAG | 9399 |
| TATTCCATAG TGTATATGTG CCACATTTTC TTAATCCAGT CTATCGTTGT | 9449 |
| TGGACATTTG GGTTGGTTCC AAGTCTTTGC TATCGTGAAT AATGCCGCAA | 9499 |
| TAAACATACG TGTGCACGTG TCTTTATAGC AGCATGATTT ATAGTCCTTT | 9549 |
| GGGTATATAC CCAGTAATGG GATGGCTGGG TCAAATGGTA CAATTGCTTC | 9599 |
| TTAAATCTTT CCCCACGGAA ACCTTGAGTG ACTGAAATAA ATATCAAATG | 9649 |
| GCGAGAGACC GTTTAGTTCG TATCATCTGT GGCATGTAGG TCAGTGATGC | 9699 |
| TCAGCATGGG TGTGAGTAAG ATGCCTGTGC TATGCATGCT CCCTGCCCCA | 9749 |
| CTGTCAGTCT TCATGAGCCA CTATTTCTAA TAAGACTGTA GACACACATA | 9799 |
| CGATATAATC ATCTCTAATC ATATCAAATG TTACATGTAA GTTTCAGCTT | 9849 |
| TAGAGACATG AATTGATAAG ATTTAAAGTT GAAAGACCAT GACTCTAGTA | 9899 |
| CTTCCTGAGT AATCAACTGA AGTATGCTTT ACACATGTGT TTTCCAAATT | 9949 |
| GCTGACTGTT AATTGTAAGT GCTTGTGACT TGAAAGGAAG CACATGATGT | 9999 |
| TCAGGGAGGA AATTCCTTTT AAATTCTGCA GGTCTACGCT CAAAGTTTAT | 10049 |
| GCAGAGGTTC AATTGCGTGT AAGACACGGG ATCACCCATA GGGTTCTGTT | 10099 |
| TTTAGTCCAT TTAATAAAAC CCAAACTGTA GTGTGCTTTG TATGCCTTTA | 10149 |
| GGGTCATCTG AATAATCTGT TGCTAAGTCA TGTTCCCAAT CGTTGTGTTT | 10199 |
| CTGTTACAGG TGAAAAGCAA TCACAGTGTT AAAAGAAGGC ACGTTGAAAT | 10249 |
| GATGCAGGCT GCTCCTATGT TGGAAATTTG TTCATTAAAA TTCTCCCAAT | 10299 |
| AAAGCTTTAC AGCCTTCTGC AAAGAAGTCT TGCGCATCTT TTGTGAAGTT | 10349 |
| TATTTCTAGC TTTTTGATGC TGTGAAATAT GTATCATTCT TTGAAATCGT | 10399 |
| GTATTGTAAC TCTCTGAGCT GGTATGTAGA GACATCGTTC TTTTTTTTTT | 10449 |
| TCTTTCTTTC TTTGTCCTCT TTTGAGACGG AGTCTTGCTC TGTCGCCCAG | 10499 |
| GCTGGAGTGC AGTGGCGCGA TCTCTGCTCA CTGCAACCCC GCCTCCCGGA | 10549 |
| TTCAAGCAAT TGTCTGCCTC AGCCTCCCGA GTAGCTGGGA TTATAGGCAC | 10599 |
| CCACCAGCAC GCCCTGGCTA AGTTTTGTGT TTTTACTAGA GATGGTTTCG | 10649 |
| CATCTTGGCC GGGGTGCTCT TGAACTCCTG ACCTCGTGAT TCACCTGCCT | 10699 |
| TGGCCTCCCA AAGTGCTGGG ATTACAGGCA TGCACGCCTC CGCGCCCGGT | 10749 |
| GGAGACATAA TTCTTACATA TTGGTTTTCT ATCCAGCGGC CTTGTGAAAT | 10799 |
| ATGCTTGTGA ATTCTAAAGT TTACTTCTAG GTCGTTTTCA GTCTTCAATA | 10849 |
| TACAGAAACA TATCATCCTG GAATAAGAGC AGTTTTGTTT CCGCCATTTT | 10899 |
| TTTTTGTTTT TCCTTTTGTA CTTTTTTTGT AGAGACGGGG TTTTGCCATG | 10949 |
| TTTCCCGGGC TGTTGTTGNN NTTTTGAGTG CAAGTGATGC ACCCACGTCA | 10999 |
| CCTCCCACAG TGCTGGGATT ACTGGCGTGG GCCAGGGGCC ACCCGTGGCG | 11049 |
| GGCCCCGTCG TTGCCATTGT AAAGAGTTTT ATTTCCTTTT CTGATTTTAT | 11099 |
| GGCATTGCGC AGACCCACCC GTTACAATGG TGACAGTGGA CATCCTTGTC | 11149 |
| TTATCCCTGA TGAGAAACCG AAAAATTTCA ACATTTCGCC ATCCTATTCA | 11199 |

-continued

| | |
|---|---|
| CTCTCCTTTT TTTGTAGACG GACTTTATCA GAGTGAGTCA TTGCATTCTG | 11249 |
| TTCCAAATTT GCTGAGAGTA TTCATTTGAA TATATGTTGA TTTTCATCAA | 11299 |
| ACAGTGCATC TATTTCGATT ACCACAGCGT TTTTTCCCAT TCATGGGTTA | 11349 |
| ATATAGTGAA TTCGATTGAT AAATTTGTAC GTTTTTAGGT TCGATTATTA | 11399 |
| AAACTTGAGA CAGCGTCTCA CTCTGTCACC GAGGCTGGAG TGCGGTGGTG | 11449 |
| TTATCAGAGC TC | 11461 |

ISOLATED, NUCLEIC ACID MOLECULES WHICH CODE FOR GAGE TUMOR REJECTION ANTIGEN, THE TUMOR REJECTION ANTIGEN, AND USES THEREOF

RELATED APPLICATION

This application is a continuation-in-part of Ser. No. 08/531,662, filed Sep. 21, 1995, now U.S. Pat. No. 5,858,689 which is a continuation-in-part of Ser. No. 08/370,648 filed Jan. 10, 1995, now U.S. Pat. No. 5,648,226 which is a continuation-in-part of patent application Ser. No. 08/250,162 filed on May 27, 1994 now U.S. Pat. No. 5,610,013, which is a continuation-in-part of Ser. No. 08/096,039 filed Jul. 22, 1993, now abandoned. All of these applications are incorporated by reference.

FIELD OF THE INVENTION

This invention relates to a nucleic acid molecule which codes for a tumor rejection antigen precursor. More particularly, the invention concerns genes, whose tumor rejection antigen precursor is processed, inter alia, into at least one tumor rejection antigen that is presented by HLA-Cw6 molecules. The genes in question do not appear to be related to other known tumor rejection antigen precursor coding sequences. The invention also relates to peptides presented by the HLA-Cw6 molecules, and uses thereof. Also a part of the inventions are peptides presented by HLA-A29 molecules, and uses thereof.

BACKGROUND AND PRIOR ART

The process by which the mammalian immune system recognizes and reacts to foreign or alien materials is a complex one. An important facet of the system is the T lymphocyte, or "T cell" response. This response requires that T cells recognize and interact with complexes of cell surface molecules, referred to as human leukocyte antigens ("HLAs"), or major histocompatibility complexes ("MHCs"), and peptides. The peptides are derived from larger molecules which are processed by the cells which also present the HLA/MHC molecule. See in this regard Male et al., Advanced Immunology ) (J. P. Lipincott Company, 1987), especially chapters 6–10. The interaction of T cells and HLA/peptide complexes is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system's response to foreign materials, in autoimmune pathologies, and in responses to cellular abnormalities. Much work has focused on the mechanisms by which proteins are processed into the HLA binding peptides. See, in this regard, Barinaga, Science, 257: 880 (1992); Fremont et al., Science 257: 919 (1992); Matsumura et al., Science 257: 927 (1992); Latron et al., Science 257: 964 (1992). Also see Engelhard, Ann. Rev. Immunol. 12: 181–207 (1994).

The mechanism by which T cells recognize cellular abnormalities has also been implicated in cancer. For example, in PCT application PCT/US92/04354, filed May 22, 1992, published on Nov. 26, 1992, and incorporated by reference, a family of genes is disclosed, which are processed into peptides which, in turn, are expressed on cell surfaces, which can lead to lysis of the tumor cells by specific CTLs cytolytic T lymphocytes, or "CTLs" hereafter. The genes are said to code for "tumor rejection antigen precursors" or "TRAP" molecules, and the peptides derived therefrom are referred to as "tumor rejection antigens" or "TRAs". See Traversari et al., Immunogenetics 35: 145 (1992); van der Bruggen et al., Science 254: 1643 (1991), for further information on this family of genes. Also, see U.S. patent application Ser. No. 07/807/043, filed Dec. 12, 1991, now U.S. Pat. No. 5,342,774.

In U.S. patent application Ser. No. 07/938,334, now U.S. Pat. No. 5,405,940, the disclosure of which is incorporated by reference, it is explained that the MAGE-1 gene codes for a tumor rejection antigen precursor which is processed to nonapeptides which are presented by the HLA-A1 molecule. The reference teaches that given the known specificity of particular peptides for particular HLA molecules, one should expect a particular peptide to bind to one HLA molecule, but not to others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. patent application Ser. No. 08/008,446, filed Jan. 22, 1993 and incorporated by reference, the fact that the MAGE-1 expression product is processed to a second TRA is disclosed. This second TRA is presented by HLA-C clone 10 molecules. The disclosure shows that a given TRAP can yield a plurality of TRAs.

U.S. patent application Ser. No. 994,928, filed Dec. 22, 1992, and incorporated by reference herein teaches that tyrosinase, a molecule which is produced by some normal cells (e.g., melanocytes), is processed in tumor cells to yield peptides presented by HLA-A2 molecules.

In U.S. patent application Ser. No. 08/032,978, filed Mar. 18, 1993, and incorporated by reference in its entirety, a second TRA, not derived from tyrosinase is taught to be presented by HLA-A2 molecules. The TRA is derived from a TRAP, but is coded for by a non-MAGE gene. This disclosure shows that a particular HLA molecule may present TRAs derived from different sources.

In U.S. patent application Ser. No. 08/079,110, filed Jun. 17, 1993 and incorporated by reference herein, an unrelated tumor rejection antigen precursor, the so-called "BAGE" precursor is described. The BAGE precursor is not related to the MAGE family.

The work which is presented by the papers, patents, and patent applications cited supra deals, in large part, with the MAGE family of genes, and the unrelated BAGE gene. It has now been found, however, that additional tumor rejection antigen precursors are expressed by cells. These tumor rejection antigen precursors are referred to as "GAGE" tumor rejection antigen precursors. They do now show homology to either the MAGE family of genes or the BAGE gene. Thus the present invention relates to genes encoding such TRAPs, the tumor rejection antigen precursors themselves as well as applications of both.

Thus, another feature of the invention are peptides which are anywhere from 9 to 16 amino acids longs, and comprise the sequence:

Xaa$_{(1,2)}$ Trp Xaa Xaa Xaa Xaa Xaa Tyr
(SEQ ID NO: 26)
where Xaa is any amino acid and Xaa$_{(1,2)}$ means that 1 or 2 amino acids may be N-terminal to the Trp residue. These peptides bind to, and/or processed to peptide which bind to HLA-A29 molecules.

The invention is elaborated upon further in the disclosure which follows.

BRIEF DESCRIPTION OF THE FIGURES

FIGS. 4A and 4B present an alignment of the cDNAs of the six GAGE genes discussed herein. In the figure, identical regions are surrounded by boxes. Translation initiation sites and stop codons are also indicated. Primers, used in polymerase chain reaction as described in the examples, are indicated by arrows.

FIG. 5 sets forth the alignment of deduced amino acid sequences for the members of the GAGE family. Identical regions are shown by boxes, and the antigenic peptide of SEQ ID NO: 4, is shown.

FIG. 7 compares the stimulation of CTL 22/23 by COS-7 cells, transfected with HLA-A29 cDNA, a MAGE, BAGE, or GAGE sequence, as shown. Control values are provided by MZ22MEL.43 and COS cells, as stimulators.

DETAILED DESCRIPTION OF PREFERRED EMBODIMENTS

Example 1

Figure 1A:
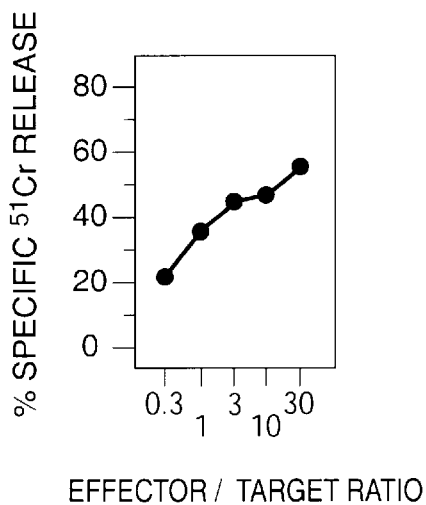
FIG. 1A–1D sets forth lysis studies using CTL clone 76/6.
Figure 1B:
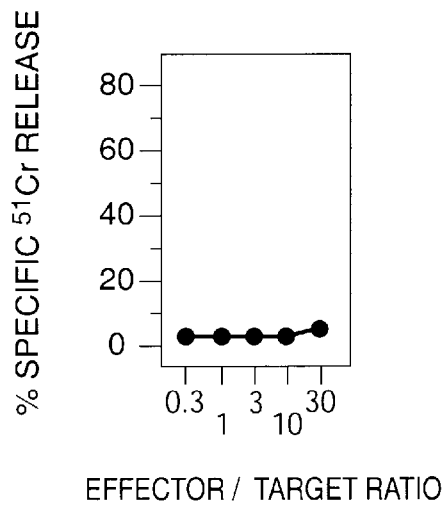
Figure 1C:
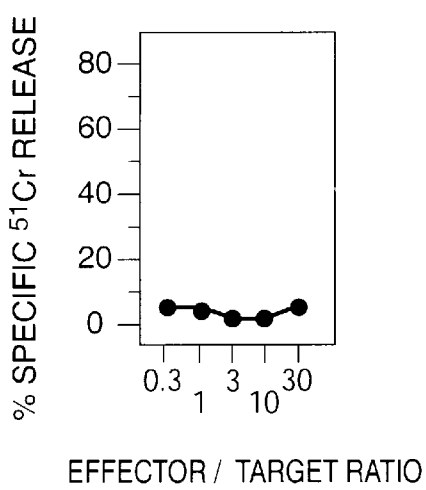
Figure 1D:
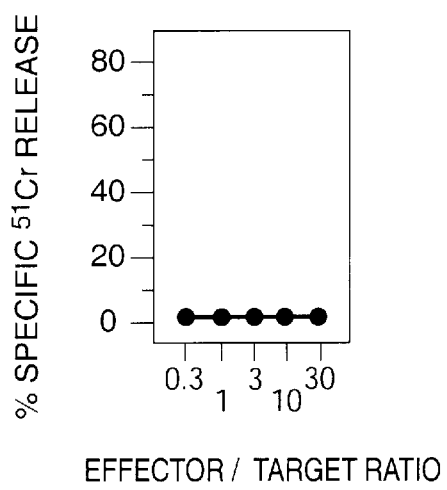

A melanoma cell line, MZ2-MEL was established from melanoma cells taken from patient MZ2, using standard methodologies. This cell line is described, e.g., in PCT application PCT/US92/04354, filed May 22, 1992, published Nov. 26, 1992, and incorporated by reference in its entirety. Once the cell line was established, a sample thereof was irradiated, so as to render it non-proliferative. These irradiated cells were then used to isolate cytolytic T cell clones ("CTLs") specific thereto.

A sample of peripheral blood mononuclear cells ("PBMSs") was taken from patient MZ2, and contacted to the irradiated melanoma cells. The mixture was observed for lysis of the melanoma cells, which indicated that CTLs specific for a complex of peptide and HLA molecule presented by the melanoma cells were present in the sample.

The lysis assay employed was a chromium release assay following Herin et al., Int. J. Cancer 39:390–396 (1987), the disclosure of which is incorporated by reference. The assay, however, is described herein. The target melanoma cells were grown in vitro, and then resuspended at $10^7$ cells/ml in DMEM, supplemented with 10 mM HEPES and 30% FCS, and incubated for 45 minutes at 37° C. with 200 $\mu$Ci/ml of Na($^{51}$Cr)O$_4$. Labelled cells were washed three times with DMEM, supplemented with 10 mM Hepes. These were then resuspended in DMEM supplemented with 10 mM Hepes and 10% FCS, after which 100 ul aliquots containing $10^3$ cells, were distributed into 96 well microplates. Samples of PBLs were added in 100 $\mu$l of the same medium, and assays were carried out in duplicate. Plates were centrifuged for 4 minutes at 100 g, and incubated for four hours at 37° C. in an 8% at CO$_2$ atmosphere.

Plates were centrifuged again, and 100 ul aliquots of supernatant were collected and counted. Percentage of $^{51}$Cr release was calculated as follows:

$$\% \ ^{51}Cr \ \text{release} = \frac{(ER - SR)}{(MR - SR)} \times 100$$

where ER is observed, experimental $^{51}$Cr release, SR is spontaneous release measured by incubating $10^3$ labeled cells in 200 ul of medium alone, and MR is maximum release, obtained by adding 100 ul 0.3% Triton X-100 to target cells.

Those mononuclear blood samples which showed high CTL activity were expanded and cloned via limiting dilution, and were screened again, again using the same methodology. The CTL clone MZ2-CTL 76/6 was thus isolated. The clone is referred to as "76/6" hereafter.

The same method was used to test target K562 cells, as well as the melanoma cell line. FIGS. 1A–1D show that this CTL alone recognizes and lyses the melanoma cell line, i.e. MZ2-MEL but not K562. The clone was then tested against other melanoma cell lines and autologous EBV-transformed B cells in the same manner described supra. FIG. 1 shows that autologous B cells, transformed by Epstein Barr Virus ("EBV") were not lysed, and that while MZ2-MEL 3.0 was lysed by CTL clone 76/6, the cell line MZ2-MEL.4F, a variant which does not express antigen F was not. Hence, the clone appears to be specific for this antigen.

The results presented supra are inconclusive as to which HLA molecule presents the TRA. The lysed cell line, i.e., MZ2-MEL, is known to express HLA-A1, HLA-A29, HLA-B37, HLA-B44, HLA-Cw6, and HLA-C clone 10. In experiments not reported here but which follow the protocol of this example, a subline of MZ2-MEL was tested, which has lost expression of HLA molecules A29, B44, and C clone 10. The subline was lysed, thus indicating that the presenting molecule should be one of A1, B37, or Cw6.

Example 2

Further studies were carried out to determine if 76/6 also produced tumor necrosis factor ("TNF") when contacted with target cells. The method used was that described by Traversari et al., Immunogenetics 35: 145–152 (1992), the disclosure of which is incorporated by reference. Briefly, samples of the CTL line were combined with samples of a target cell of interest in culture medium. After 24 hours, supernatant from the cultures was removed, and then tested on TNF-sensitive WEHI cells. Cell line MZ2-MEL.43, a subclone of the MZ2-MEL cell line discussed supra as well as in the cited references, gave an extremely strong response, and was used in the following experiments.

Example 3

The results from Example 2 indicated that MZ2.MEL.43 presented the target antigen of interest. As such, it was used as a source of total mRNA to prepare a cDNA library.

Total RNA was isolated from the cell line. The mRNA was isolated using an oligo-dT binding kit, following well recognized techniques. Once the mRNA was secured, it was transcribed into cDNA, via reverse transcription, using an oligo dT primer containing a NotI site, followed by a second strand synthesis. The cDNA was then ligated to a BstXI adaptor, digested with NotI, size fractionated on a Sephacryl S-500 HR column, and then cloned, undirectionally, into the BstXI and Not I sites of pcDNA-I-Amp. The recombinant plasmid was then electroporated into DH5α *E. coli* bacteria. A total of 1500 pools of 100 recombinant bacteria were seeded in microwells. Each contained about 100 cDNAs, because nearly all bacteria contained an insert.

Each pool was amplified to saturation and plasmid DNA was extracted by alkaline lysis and potassium acetate precipitation, without phenol extraction.

Example 4

Following preparation of the library described in Example 3, the cDNA was transfected into eukaryotic cells. The transfections, described herein, were carried out in duplicate. Samples of COS-7 cells were seeded, at 15,000 cells/well into tissue culture flat bottom microwells, in Dulbecco's modified Eagles Medium ("DMEM") supplemented with 10% fetal calf serum. The cells were incubated overnight at 37° C., medium was removed and then replaced by 50 µl/well of DMEM medium containing 10% Nu serum, 400 µg/ml DEAE-dextran, and 100 µM chloroquine, plus 100 ng of the plasmids. As was indicated supra, the lysis studies did not establish which HLA molecule presented the antigen. As a result, cDNA for each of the HLA molecules which could present the antigen (A1, B37, Cw6) was used, separately, to cotransfect the cells. Specifically, one of 28 ng of the gene encoding HLA-A1, cloned into pCD-SRα was used, as were 50 ng of cDNA for HLA-B37 in pcDNA-I-Amp, or 75 ng of cDNA for HLA-Cw6 in pcDNAI/Amp, using the same protocol as was used for transfection with the library.

Transfection was made in duplicate wells, but only 500 pools of the HLA-Cw6 transfectants could be tested in single wells. Following four hours of incubation at 37° C., the medium was removed, and replaced by 50 µl of PBS containing 10% DMSO. This medium was removed after two minutes and replaced by 200 µl of DMEM supplemented with 10% FCS.

Following this changed in medium, COS cells were incubated for 24–48 hours at 37° C. Medium was then discarded, and 1000–3000 cells of CTL clone 76/6 were added, in 100 µl of Iscove's medium containing 10% pooled human serum supplemented with 20–30 U/ml of IL-2. Supernatant was removed after 24 hours, and TNF content was determined in an assay on WEHI cells, as described by Traversari et al., Immunogenetics 35: 145–152 (1992), the disclosure of which is incorporated by reference.

The 1500 pools transfected with HLA-A1, and the 1500 pools transfected with HLA-B37 stimulated TNF release to a concentration of 15–20 pg/ml, or 2–6 pg/ml, respectively. Most of the HLA-Cw6 transfectants yielded 3–20 pg/ml, except for one pool, which yielded more than 60 pg/ml. This pool was selected for further work.

Example 5

Figure 2:
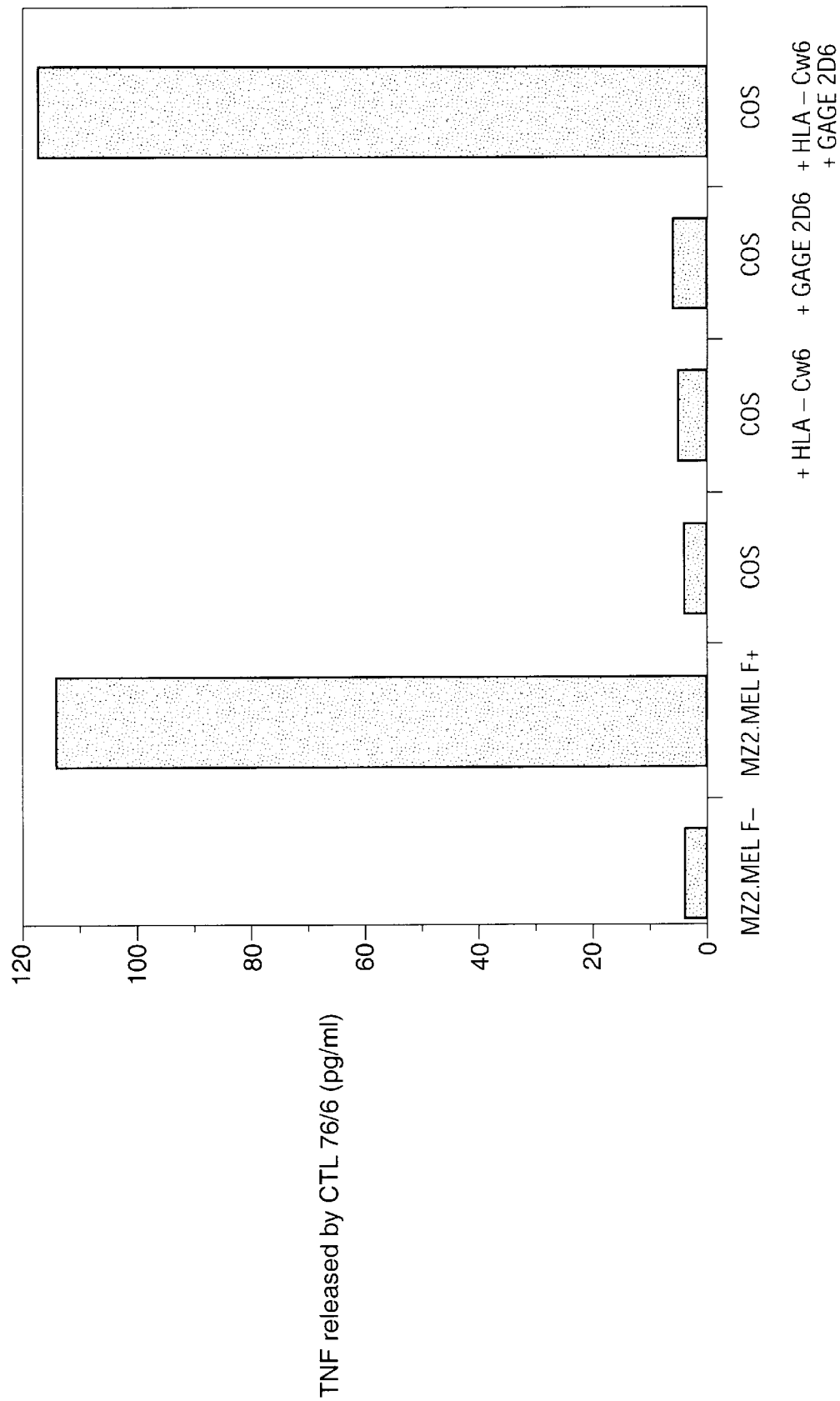
FIG. 2 shows tumor necrosis factor ("TNF") release assays obtained with various transfectants and controls.

The bacteria of the selected pool were cloned, and 600 clones were tested. Plasmid DNA was extracted therefrom, transfected into a new sample of COS cells in the same manner as described supra, and the cells were again tested for stimulation of CTL clone 76/6. Ninety-four positive clones were found. One of these, referred to as cDNA clone 2D6, was tested further. In a comparative test COS cells were transfected with cDNA clone 2D6 and the HLA-Cw6 cDNA, HLA-Cw6 cDNA alone, or cDNA 2D6 alone. Control cell lines MZ2-MEL F and MZ2-MEL F+ were also used. TNF release into CTL supernatant was measured by testing it on WEHI cells, as referred to supra. The number of surviving WEHI cells was measured by optical density after incubation of the cells with MTT. FIG. 2 shows that the COS cells transfected with HLA-Cw6 and cDNA-2N6, and the cell line MZ2-MEL F+ stimulated TNF release from CTL clone 76/6, indicating that HLA-Cw6 presented the subjected TRA.

Example 6

The cDNA 2N6 was sequenced following art known techniques. A sequence search revealed that the plasmid insert showed no homology to known genes or proteins. SEQ ID NO: 1 presents cDNA nucleotide information for the identified gene, referred to hereafter as "GAGE". A putative open reading frame is located at bases 51–467 of the molecule. The first two bases of this sequence are from the vector carrying the cDNA sequence, and are thus not part of the cDNA itself.

Example 7

Following sequencing of the cDNA, as per Example 6, experiments were carried out to determine if cells of normal tissues expressed the gene. To determine this, Northern blotting was carried out on tissues and tumor cell lines, as indicated below. The blotting experiments used cDNA for the complete sequence of SEQ ID NO: 1. PCR was then used to confirm the results.

TABLE 1

| Expression of gene GAGE | |
|---|---|
| Normal tissues | |
| PHA activated T cells | – |
| CTL clone 82/30 | – |
| Liver | – |
| Muscle | – |
| Lung | – |
| Brain | – |
| Kidney | – |
| Placenta | – |
| Heart | – |
| Skin | – |
| Testis | + |
| Tumor cell lines | |
| Melanoma | 7/16 |
| Lung Carcinoma | 1/6 |
| Sarcoma | 0/1 |
| Thyroid medullary carcinoma | 0/1 |
| Tumor samples | |
| Melanoma | 1/1 |

Example 8

Detailed analysis of normal tissues and tumors was carried out by applying polymerase chain reaction ("PCR")and the GAGE gene information described supra.

First, total RNA was taken from the particular sample, using are recognized techniques. This was used to prepare cDNA. The protocol used to make the cDNA involved combining 4 ul of reverse transcriptase buffer 5×, 1 ul of each dNTP, (10 mM), 2 ul of dithiothreitol (100 mM), 2 ul of dT-15 primer (20 um), 0.5 µl of RNasin (40 units/ul), and 1 ul of MoMLV reverse transcriptase (200 units/ul). Next 6.5 ul of template RNA (1 μg/3.25 ul water, or 2 ug total template RNA) was added. The total volume of the mixture was 20 ul. This was mixed and incubated at 42° C. for 60 minutes, after which it was chilled on ice. A total of 80 ul of water was then added, to 100 ul total. This mixture was stored at −20° C. until used in PCR.

To carry out PCR, the primers

5'-AGA CGC TAC GTA GAG CCT-3'
(sense)
and
5'-CCA TCA GGA CCA TCT TCA-3'
(antisense)

SEQ ID NOS: 2 and 3, respectively, were used. The reagents included 30.5 ul water, 5 ul of PCR buffer 10×, 1 ul of each dNTP (10 uM), 2.5 ul of each primer (20 uM), and 0.5 ul of polymerizing enzyme "Dynazyme (2 units/ul). The total volume was 45 ul. A total of 5 ul of cDNA was added (this corresponded to 100 ng total RNA). The mixture was combined, and layered with one drop of mineral oil. The mixture was transferred to a thermocycler block, preheated to 94° C., and amplification was carried out for 30 cycles, each cycle consisting of the following:

first denaturation: 94° C., 4 min.
denaturation: 94° C., 1 min.
annealing: 55° C., 2 min.
extension: 72° C., 3 min.
final extension: 72° C., 15 min.

Following the cycling, 10 ul aliquots were run on a 1.5% agarose gel, stained with ethidium bromide.

cDNA amplified using the primers set forth supra yields a 238 base pair fragment. There is no amplification of contaminating genomic DNA, if present.

The results are presented in Table 2, which follows. They confirm that the only normal tissue which expresses GAGE is testes, whereas a number of tumors, including melanoma, lung, breast, larynx, pharynx, sarcoma, testicular seminoma, bladder and colon express the gene. Thus, any one of these tumors can be assayed for by assaying for expression of the GAGE gene.

TABLE 2

RT-PCR analysis of the expression of gene GAGE

| NORMAL TISSUES | | |
| --- | --- | --- |
| Heart | – | |
| Brain | – | |
| Liver | – | |
| Lung | – | |
| Kidney | – | |
| Spleen | – | |
| Lymphocytes | – | |
| Bone marrow | – | |
| Skin | – | |
| Naevus | – | |
| Melanocytes | – | |
| Fibroblasts | – | |
| Prostate | – | |
| Testis | + | |
| Ovary | – | |
| Breast | – | |
| Adrenals | – | |
| Muscle | – | |
| Placenta | – | |
| Umbilical Cord | – | |
| TUMORS | Cell lines | Tumor samples |
| Melanoma | 40/63 | 46/146 (32%) |

TABLE 2-continued

RT-PCR analysis of the expression of gene GAGE

| Lung cancer | | |
| --- | --- | --- |
| Epidermoid carcinoma | | 10/41 (24%) |
| Adenocarcinoma | | 4/18 |
| Small Cell Lung Cancer | 6/23 | 0/2 |
| Breast cancer | | 15/146 (10%) |
| Head and Neck tumor | | |
| Larynx | | 6/15 (40%) |
| Pharynx | | 3/13 |
| Sarcoma | 1/4 | 6/18 (33%) |
| Testicular seminoma | | 6/6 (100%) |
| Bladder cancer | | 5/37 (14%) |
| Prostate cancer | | 2/20 |
| Colon carcinoma | 5/13 | 0/38 |
| Renal cancer | 0/6 | 0/45 |
| Leukemia | 3/6 | 0/19 |

Example 9

The identification of the nucleic acid molecule referred to in the prior examples led to further work directed to the determination of tumor rejection antigens presented by HLA-Cw6 molecules, and derived from the GAGE gene.

The complete cDNA of GAGE in expression vector pcDNAI/Amp was digested with restriction endonucleases NotI and SphI, and then with exonuclease III following supplier's instruction (Erase-a-base System, Promega). This treatment generated a series of progressive deletions, starting the 3'end.

The deletion products were ligated back into pcDNAI/Amp, and then electroporated into E. coli strain DH5α'IQ, using well known techniques. The transformants were selected with ampicillin (50 micrograms/ml).

Plasmid DNA was extracted from each recombinant clone and was then transfected into COS-7 cells, together with a vector which coded for HLA-Cw6. The protocols used follow the protocols described above.

The transfectants were then tested in the TNF release assay. This permitted separation of positive and negative clones. All the negative clones showed a deletion of the entire GAGE sequence. The smallest positive clone contained the first 170 nucleotides of SEQ ID NO: 1. The analysis of this sequence, supra, notes that the open reading frame starts at nucleotide 51. Thus, this fragment contains a sequence which encodes the first 40 amino acids of the GAGE TRAP.

Example 10

Additional experiments were then carried out to define the region encoding the TRA peptide more precisely. Polymerase chain reaction ("PCR") amplification was used to do this.

Two primers were synthesized. The first primer was a 22-mer complementary to a sequence within the plasmid vector pcDNAI/Amp located upstream of a BamHI site. The second primer was a 29-mer containing the 3'end nucleotides 102–119 of SEQ ID NO: 1, and at the 5'end an extension of 11 nucleotides containing an XbaI restriction site.

Following amplification, the PCR product was digested by BamHI and XbaI, and cloned into the BamHI-XbaI sites of plasmid pcDNA-3. The recombinant colonies were cotransfected into COS-7 cells with cDNA encoding HLA- Cw6, in accordance with Example 4, and a TNF release assay, also as described supra, was carried out, using CTL 76/6.

TNF release was observed, indicating that the "minigene" was processed to a TRA. The minigene, i.e., nucleotides 1–119 of SEQ ID NO: 1, the coding region of which runs from nucleotides 51–119 encoded the first 23 amino acids of the cDNA of SEQ ID NO: 1. This information served as the basis for the next set of experiments.

Example 11

Two peptides were synthesized, based upon the first 23 amino acids encoded by SEQ ID NO: 1. These were:
Met Set Trp Arg Gly Arg Ser Thr tyr Arg Pro Arg Pro Arg Arg (SEQ ID NO: 12)
and
Thr Tyr Arg Pro Arg Pro Arg Arg Tyr Val Glu Pro Pro Glu Met Ile (SEQ ID NO: 13)

Each peptide was pulsed into COS-7 cell previously transfected with HLA-Cw6 cDNA, and combined with CTL 76/6 to determine if TNF release would be induced. Peptides (20 ug/ml) were added to COS-7 cells which had been transfected with the HLA-Cw6 cDNA twenty-four hours previously. After incubation at 37° for 90 minutes, medium was discarded, and 3000 CTLs were added in 100 microliters of medium, containing 25 units/ml of IL-2. Eighteen hours later, TNF content of supernatant was tested via determining toxicity on WEHI-164-13 cells. The second peptide (SEQ ID NO: 3) was found to induce more than 30 pg/ml of TNF, while the first peptide (SEQ ID NO: 2), was found to induce less than 10 pg/ml of TNF. The second peptide was used for further experiments.

Example 12

Figure 3:
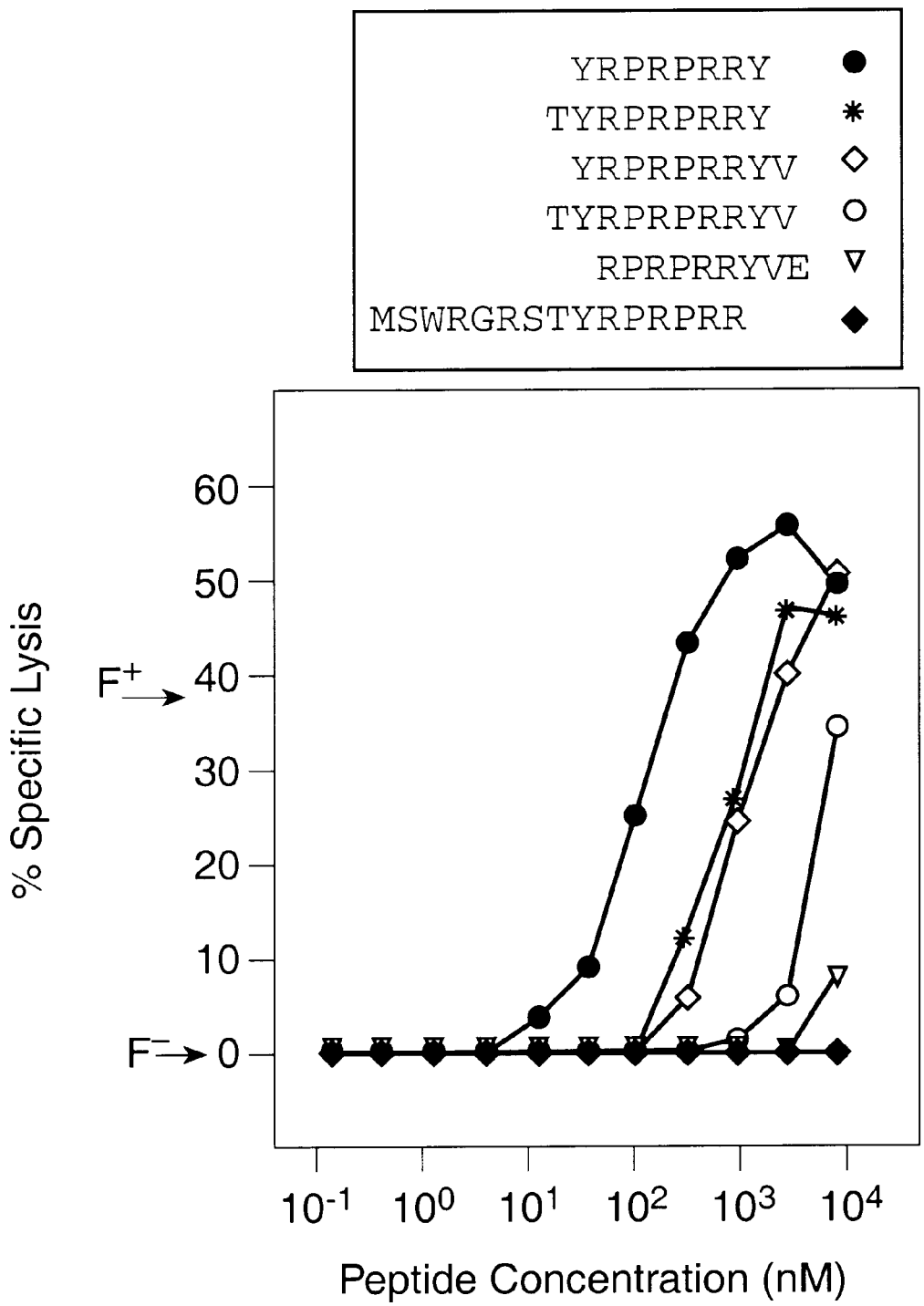
FIG. 3 compares lysis induced by cytoloytic T lymphocytes of clone CTL 76/6. Peptides of varying length were tested, including SEQ ID NO: 4.
Figure 6:
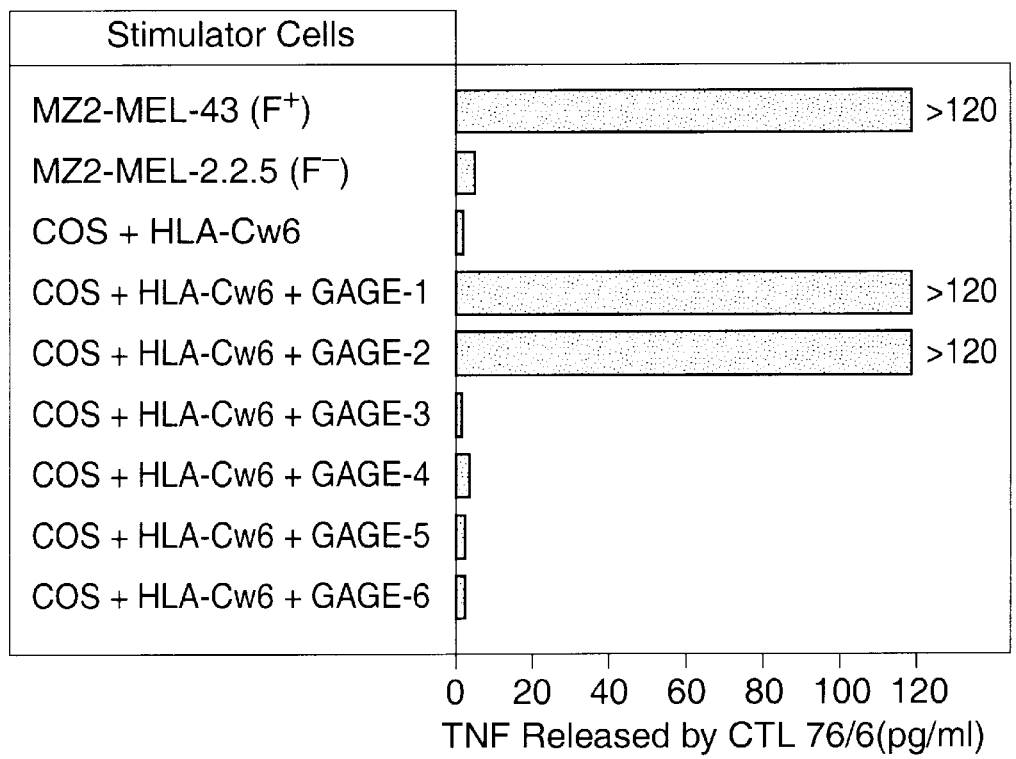
FIG. 6 shows the results obtained when each of the GAGE cDNAs was transfected into COS cells, together with HLA-Cw6 cDNA. Twenty-four hours later, samples of CTL 76/6 were added, and TNF release was measured after twenty-four hours.

Various peptides based upon SEQ ID NO: 3 were synthesized, and tested, some of which are presented below. To carry out these tests, $^{51}$Cr labelled LB33-EBV cells, which are HLA-Cw6 positive, were incubated with one of the following peptides:
Tyr Arg Pro Arg Pro Arg Arg Tyr
  (SEQ ID NO: 4)
Thr Tyr Arg Pro Arg Pro Arg Arg Tyr
  (SEQ ID NO: 5)
Tyr Arg pro Arg Pro Arg Arg Tyr Val
  (SEQ ID NO: 6)
Thr Tyr Arg Pro Arg Pro Arg Arg Tyr Val
  (SEQ ID NO: 7)
Arg Pro Arg Pro Arg Arg Tyr Val Glu
  (SEQ ID NO: 8)
Met Ser Trp Arg Gly Arg Ser Thr Tyr Arg Pro Arg Pro Arg Arg
  (SEQ ID NO: 12)
The peptide concentration varied, as indicated in FIG. 3, and the ratio of CTL: LB3-EBV ("effector: target ratio"), was 10:1. $^{51}$Cr release was determined after four hours of incubation at 37° C. Levels of lysis for positive ("F$^{+}$", MZ2-MEL.3.1), and negative ("F", MZ2-MEL.2.2.5) control cells are indicated, in FIG. 3.

It was found, quite surprisingly, that the octamer of SEQ ID NO: 4 was the best peptide, and appeared to be the tumor rejection antigen. This is the first time an octamer has been reported as being involved in presentation by a human MHC molecule. There is some precedent for a murine system, as reported by Engelhard, supra, at 199, for H-2K$^{b}$ and H-2K$^{K}$ molecules. The nonamers of SEQ ID NO: 5 and SEQ ID NO: 6 also induced CTL lysis albeit to a lesser extent than the octamer of SEQ ID NO: 4.

In results not reported here, a second CTL was tested (CTL 82/31). This CTL was known to lyse cells presenting MZ2-F. It, too, lysed HLA-Cw6 positive cells following pulsing with the peptide of SEQ ID NO: 4.

Example 13

Figure 4A:
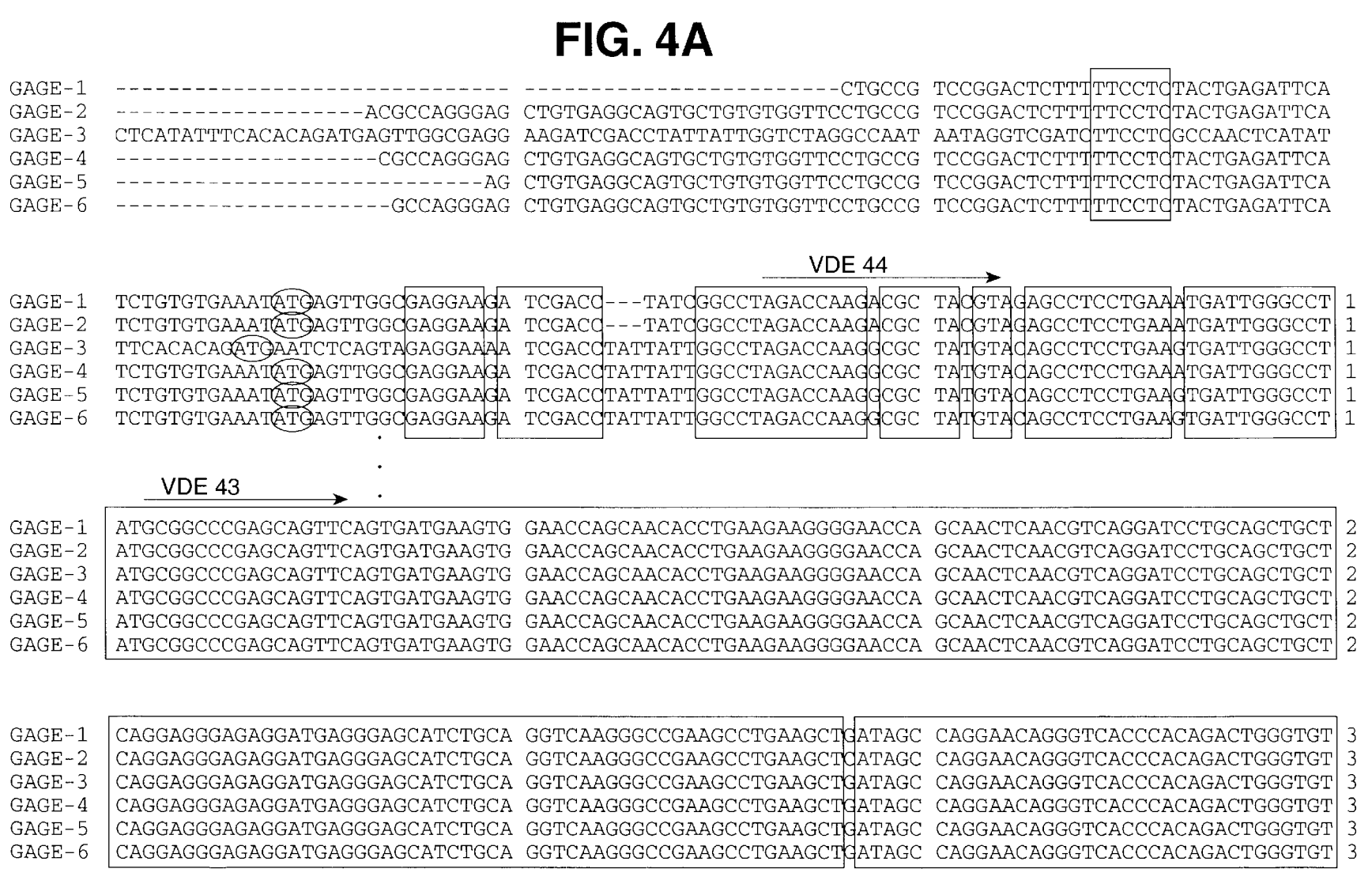
Figure 4B:
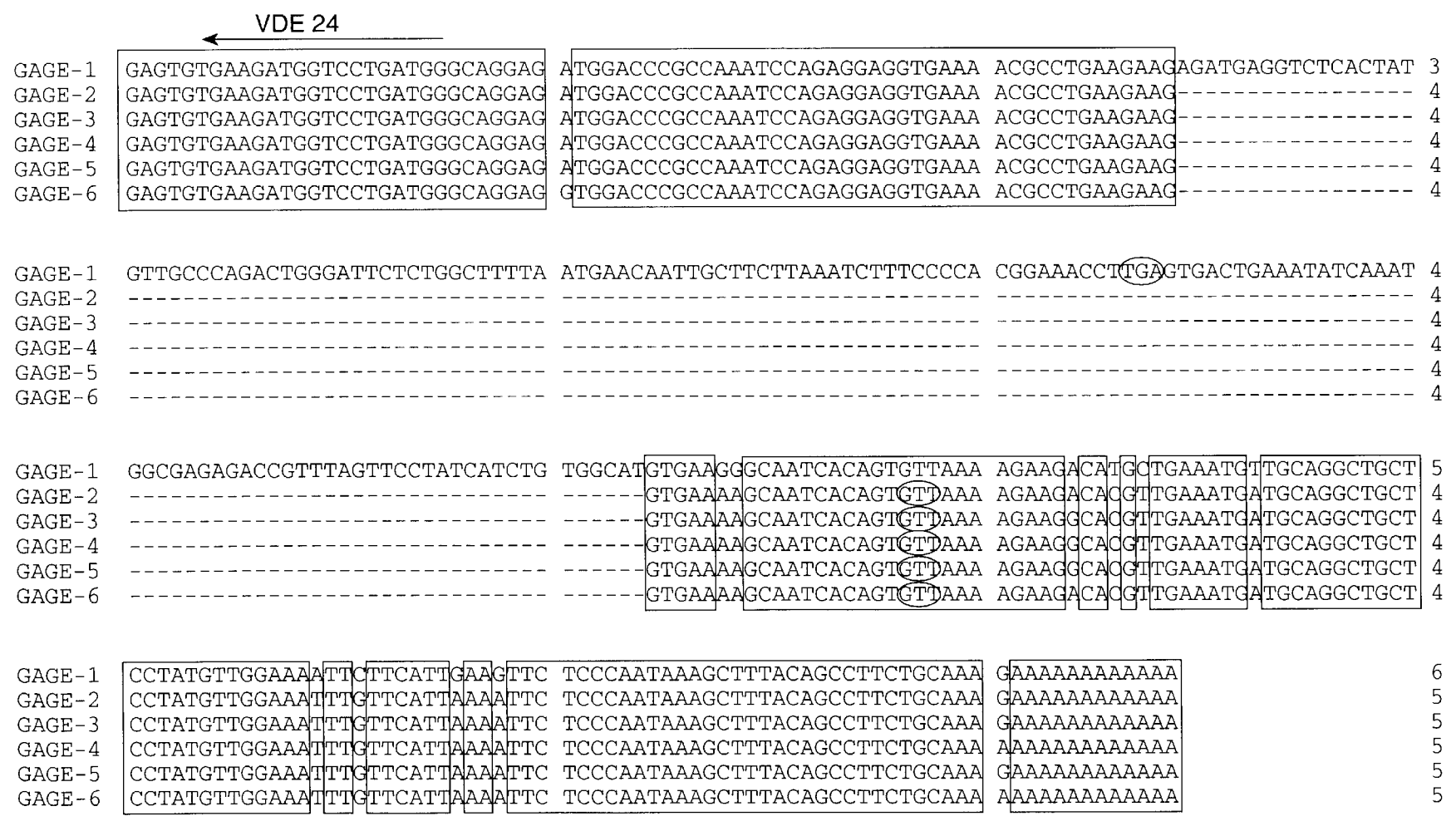

To find out whether the GAGE DNA set forth supra was unique, a cDNA library made with RNA from MZ2-MEL.43 (the same library that was used for the cloning of GAGE) was hybridized with a probe derived from the GAGE cDNA. The probe was a PCR fragment of 308 base pairs between positions 20 and 328 of SEQ ID NO: 1. Twenty positive cDNAs were obtained. Six of them were entirely sequenced. They were all highly related to the GAGE sequence, but they were slightly different from it. Two of the six clones were identical to each other, but all the others differed from each other. Thus, five new sequences different from but highly related to GAGE were identified. They are called GAGE-2, 3, 4, 5 and 6 (FIGS. 4A and 4B). The fourteen other clones were partially sequenced at the 5' end and their sequence corresponded to one of the six GAGE cDNAs.

The major difference between these cDNAs and GAGE-1 is the absence of a stretch of 143 bases located at position 379 to 521 of the GAGE sequence of SEQ ID NO: 1. The rest of the sequences shows mismatches only at 19 different positions, with the exception of GAGE-3 whose 5'end is totally different from the other GAGE for the first 112 bases. This region of the GAGE-3 cDNA contains a long repeat and a hairpin structure.

The deduced GAGE-1 protein corresponding to a tumor rejection antigen precursor is about 20 amino acids longer than the 5 other proteins, whose last seven residues also differ from the homologous residues of GAGE-1 (FIG. 5). The rest of the protein sequences show only 10 mismatches. One of these is in the region corresponding to the antigenic peptide of SEQ ID NO: 4. The sequence of the peptide is modified in GAGE-3, 4, 5 and 6 so that position 2 is W instead of R.

Example 14

To assess whether the change at position 2 affected the antigenicity of the peptide, cDNA of the 6 GAGE cDNAs were individually transfected into COS cells together with the cDNA of HLA-Cw6, and the transfectants were tested for recognition by CTL 76/6 as described, supra. Only GAGE-1 and GAGE-2 transfected cells were recognized, showing that the modified peptide encoded by GAGE-3, 4, 5 and 6 was not antigenic in the context of this experiment. Sequence analysis of the 5' end of the 14 other clones mentioned supra, showed that 7 of them contained the sequence encoding the antigenic peptide, and thus probably corresponded to either GAGE-1 or GAGE-2.

Example 15

The PCR primers used, supra to test the expression of GAGE in tumor samples do not discriminate between GAGE-1 or 2 and the four other GAGE cDNAs that do not encode antigen MZ2F. A new set of primers was prepared which specifically amplifies GAGE-1 and 2, and not GAGE-3, 4, 5 and 6. These primers are:
  VDE44 5'-GAC CAA GAC GCT ACG TAG-3' (SEQ ID NO: 9)
VDE24 5'-CCA TCA GGA CCA TCT TCE-3' (SEQ ID NO: 10)
These primers were used as described, supra, in a RT-PCR reaction using a polymerase enzyme in the following temperature conditions:

4 min at 94° C.

30 cycles with 1 min at 94° C.

2 min at 56° C.

3 min at 72° C.

15 min at 72° C.

The results of this analysis are set forth in Table 3.

TABLE 3

Expression of GAGE genes by tumor samples and tumor cell lines

| Histological type | Number of GAGE positive tumors | |
|---|---|---|
| | All GAGE genes* | GAGE-1 and 2** |
| Tumor samples | | |
| Melanomas | | |
| primary lesions | 5/39 | 5/39 (13%) |
| metastases | 47/132 | 36/131 (27%) |
| Sarcomas | 6/20 | 6/20 (30%) |
| Lung carcinomas NSCLC | 14/65 | 12/64 (19%) |
| Head and neck aquamous cell carcinomas | 13/55 | 10/54 (19%) |
| Prostatic carcinomas | 2/20 | 2/20 |
| Mammary carcinomas | 18/162 | 14/162 (9%) |
| Bladder carcinomas | | |
| superficial | 1/20 | 1/20 |
| infiltrating | 5/26 | 3/26 |
| Testicular seminomas | 6/6 | 5/6 |
| Colorectal carcinomas | 0/43 | |
| Leukemias and lymphomas | 0/25 | |
| Renal carcinomas | 0/46 | |
| Tumor cell lines | | |
| Melanomas | 45/74 | 40/74 (54%) |
| Sarcomas | 1/4 | 1/4 |
| Lung carcinomas | | |
| SCLC | 7/24 | 7/24 (29%) |
| NSCLC | 1/2 | 1/2 |
| Mesotheliomas | 5/19 | 5/19 (26%) |
| Head and neck squamous cell carcinomas | 0/2 | |
| Mammary carcinomas | 1/4 | 0/4 |
| Bladder carcinomas | 0/3 | |
| Color carcinomas | 5/13 | 5/13 |
| Leukemias | 3/6 | 1/6 |
| Lymphomas | 0/6 | |
| Renal carcinomas | 0/6 | |

*Expression of GAGE was tested by RT-PCR on total RNA with primers VDE-18 and VDE-24, detecting all GAGE genes. No PCR product was observed when these primers were assayed on DNA from MZ2-MEL.
**Expression of GAGE-1 and 2 was tested by RT-PCR on total RNA with primers VDE-44 and VDE-24, which distinguish GAGE-1 and 2 from the four other GAGE genes. No PCR product was observed when these primers were assayed on DNA from MZ2-MEL.

In further work, new primers were designed which amplified all GAGE genes, to make sure that there was no expression of any of them in normal tissues. These primers are

VDE43 5'-GCG GCC CGA GCA GTT CA-3' (SEQ ID NO: 11)

VDE24 5'-CCA TCA GGA CCA TCT TCA-3 (SEQ ID NO: 10)

These were used exactly as for the PCR using the VDE44 and VDE24 primers. The results are shown in Table 4. They confirm that the normal tissues are negative, except for testis.

TABLE 4

Expression of GAGE genes in normal adult and fetal tissues

| | GAGE expression* |
|---|---|
| Adult tissues | |
| Adrenal gland | – |
| Benign naevus | – |
| Bone marrow | – |
| Brain | – |
| Breast | – |
| Cerebellum | – |
| Colon | – |
| Heart | – |
| Kidney | – |
| Liver | – |
| Lung | – |
| Melanocytes | – |
| Muscle | – |
| Ovary | – |
| Prostate | – |
| Skin | – |
| Splenocytes | – |
| Stomach | – |
| Testis | + |
| Thymocytes | – |
| Urinal bladder | – |
| Uterus | – |
| Placenta | – |
| Umbilical cord | – |
| Fetal tissues[a] | |
| Fibroblasts | – |
| Brain | – |
| Liver | – |
| Spleen | – |
| Thymus | – |
| Testis | + |

*Expression of GAGE was tested by RT-PCR amplification on total RNA with primers VDE43 and VDE24 detecting all GAGE genes (FIG. 7). Absence of PCR product is indicated by – and presence by +. No PCR product was observed when these primers were assayed on DNA from MZ2-MEL.
[a]Fetal tissues derive from fetuses older than 20 weeks.

Example 16

In work not reported here, it had been ascertained that cytolytic T cell clone CTL 22/23 (Van den Eynde, et al., Int. J. Cancer 44: 634–640 (1989), incorporated by reference) did not recognize melanoma cell line MZ2MEL.3.1. This melanoma cell line was reported by Van der Bruggen, et al., Eur. J. Immunol. 24: 2134–2140 (1994), to have lost expression of MHC molecules HLA-A29, HLA-B24, and HLA-cw·1601. Studies were undertaken to determine if transfection with one of these MHC molecules could render the line sensitive to CTL 22/23. HLA-A29 was the first molecule tested. To do so, poly A$^+$ RNa was extracted from HLA-A29$^+$ cell line MZ2-MEL.43, using a commercially available extraction kit, and following the manufacturer's instructions. The mRNA was then converted to cDNA, using standard methodologies, size fractionated, and then inserted unidirectionally, into the Bstx1 and NotI sites of plasmid pcDNA-I/Amp. The plasmids were electroporated into E. coli strain DH5α'IQ, and selected with ampicillin (50 μg/ml). The bacteria were plated onto nitrocellulose filters, and duplicated. The filters were prepared, and hybridized overnight in 6xSSC/0.1% SDS/1× Denhardt's solution at 40° C., using $^{32}$P labelled probe:

5'ACTCCATGAGGTATTTC-3'
(SEQ ID NO: 19)
The probe is a sequence which surrounds the start codon of HLA sequences.

The filters were washed twice, at room temperature for 5 minutes each time in 6xSSC, and twice in 6xSSC at 43° C. Positive sequences were then screened with probe:

5'-TTTCACCACATCCGTGT-3'
(SEQ ID NO: 20)
which had been labelled with $^{32}$P. This sequence is specific for HLA-A29, as determined by reference to the Kabat Database of sequences and proteins of immunological interest, incorporated by reference. This database is available at the NCBI (USA), or on Web Sotle (Internet) WWW.NCBI.NLM.NIH.GOV. The filters were washed twice at room temperature for 5 minutes each time, at 6xSSC, followed by two washes, at 6xSSC (5 minutes per wash), at 42° C.

Example 17

Once positive HLA-A29 clones were isolated, these were transfected into COS-7 using the DEAE-dextran chloroquine method set out supra. In brief, 1.5×10$^4$ COS-7 cells were treated with 50 ng of plasmid pcDNA-I/Amp containing HLA-A29, and 100 ng of cDNA containing cDNA for one of the GAGE sequences mentioned supra, or one of the prior art MAGE or BAGE sequences in plasmid pcDNAα-I/Amp or pcDSRα-respectively. The transfectants were then incubated for 24 hours at 37° C.

The tranfectants were then tested for their ability to stimulate TNF production by CTLs, using the assay explained at the end of example 4 supra.

FIG. 7, which presents the results of this drug, shows that high levels of TNF production were achieved using any of GAGE-3, 4, 5 or 6 and HLA-A29 as transfectants. GAGE-1 and GAGE-2, in contrast, do not stimulate CTL clone 22/23, thus leading to the conclusion that GAGE 3, 4, 5 and 6 are processed to an antigen or antigens presented by HLA-A29 molecules and recognized by CTL 22/23.

Example 18

The fact that GAGE-3, 4, 5 and 6 were processed to peptides presented by HLA-A29$^+$ cells, which GAGE-1 and GAGE-2 were not, suggested examination of the deduced amino acid sequences for those common to GAGE 3, 4, 5 and 6 and absent from GAGE-1 and GAGE-2. The sequence:

Arg Ser Thr Tyr Trp Pro Arg Pro Arg Arg Tyr Val Gln
(SEQ ID NO: 21)
was identified. The peptide was synthesized, lyophilized, and then dissolved in 1 volume DMSO, 9 volumes of 10 mM acetic acid in water. This methodology was used for the other peptides synthesized, discussed infra.

The peptide (SEQ ID NO: 21) was tested in a $^{51}$Cr release experiment, following the method described supra.

Figure 8:
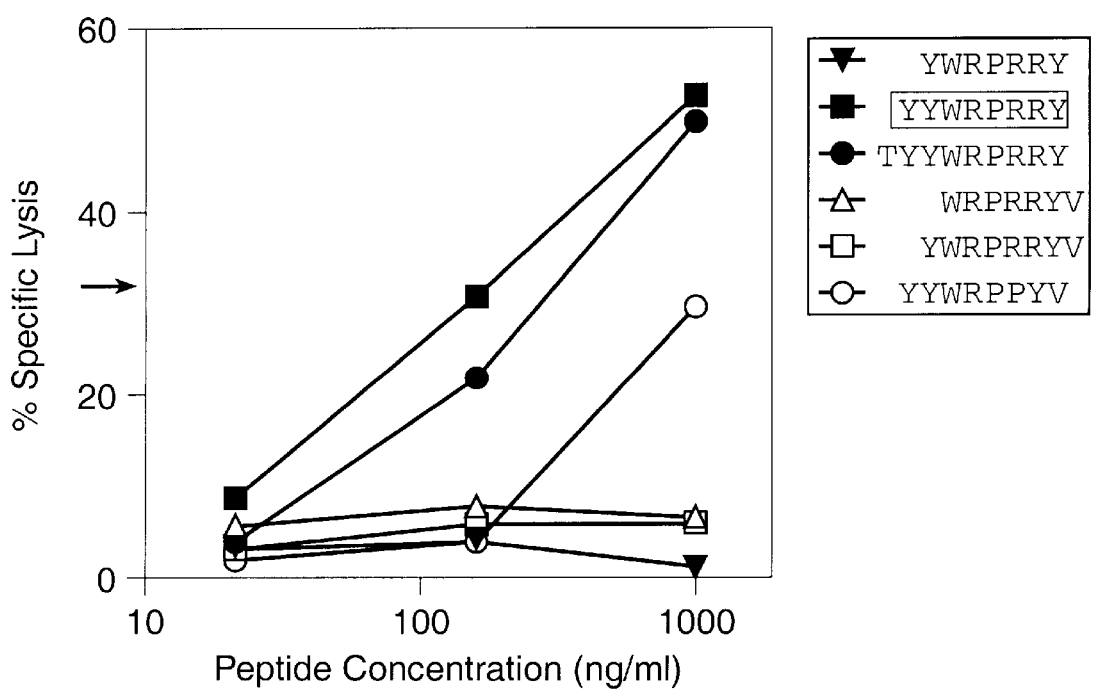
FIG. 8 presents results obtained from $^{51}$Cr release studies, using various peptides including SEQ ID NO: 22 and various peptides derived therefrom.

It was found that this peptide did provoke lysis. Successive deletions were prepared, and tested for their ability to provoke lysis, again using the $^{51}$Cr lytic assay. This work is depicted in FIG. 8. It was found that the shortest peptide to provoke lysis was Tyr Tyr Trp Pro Arg Pro Arg Arg Tyr
(SEQ ID NO: 22), which is common to all of GAGE-3 through 6. Specifically, amino acids 10–18 of GAGE-3, and amino acids 9–17 of GAGE-4, 5 and 6 correspond to this peptide.

The members of the peptide family shown in FIG. 8, and represented, e.g., by SEQ ID NOS: 21 and 22, do not accord with the data presented by Toubert, et al., "HLA-A29 Peptide Binding Motif", Abstract No. 4183, Ninth International Congress of Immunology, Jul. 23–29, 1995, San Francisco, Calif., incorporated by reference. According to Toubert, et al., at the least a Phe residue is required at the third position of any peptide which binds to HLA-A29. As is shown herein, such is not the case.

Example 19

A set of experiments were carried out to isolate and to clone genomic DNA sequences encoding GAGE TRAPS.

A library was made from genomic DNA isolated from the peripheral blood lymphocytes of patient MZ2. Isolation and preparation of the DNA was carried out in accordance with Wölfel et al., Immunogenetics 26: 178–187 (1987), incorporated by reference. The isolated DNA was then partially digested with the restriction enzyme Sau3A, and then fractionated using NaCl density gradient ultracentrifugation. This provides a fraction enriched in 10–20 kb fragments of DNA. See Grosveld et al., Nucl. Acids. Res. 10: 6715–6732 (1982). These fragments were dephosphorylated using alkaline phosphatase, and were then ligated into λ-Gem11 DNA, which had been digested with BamHI/EcoRI. Briefly, 2 ugs of the genomic DNA were mixed with 2 ugs of the λ phage DNA in a 10 ul volume, and incubated at 16° C. overnight. 4 μl of the ligation mixture containing the ligated DNA was packaged, in vitro, in a commercially available phage packaging extract. The resulting phages were titrated on E. coli NM539 (a commercially available strain), in order to calculate the appropriate number of phages to plate out for screening. The resulting product was titrated onto cells of E. coli strain NM539.

Example 20

Approximately 33,333 recombinant phages were plated per plate, to give a total of 500,000 phages tested. A total of 20 μl of the packaging mixture was mixed with 1 ml of a suspension of E. coli NM539 in 10 mM MgSO$_4$, to an OD$_{600}$ of 0.5. This mixture was then incubated, for 15 minutes at 37° C., and then mixed with 15 ml of culture medium BTCYM containing 0.7% agarose at 45° C., and then plated onto agar plates containing BTCYM. The resulting mixture was incubated, at 37° C., overnight. The resulting phage plaques were used in hybridization experiments. Approximately 500,000 recombinant phage plaques were immobilized on nylon membranes, and were then subjected to in situ hybridization, in accordance with Sambrook et al., Molecular Cloning: A Laboratory Manual (1989), incorporated by reference.

The hybridization was carried out using a probe which consisted of nucleotides 18 through 326 of SEQ ID NO: 1. The probe was prepared using the polymerase chain reaction and, as primers, a nucleotide sequence consisting of nucleotides 18–34 and the complement of nucleotides 309–326 of this sequence. The primers were used in a 30 cycle PCR run (1 cycle: 94° C. for one minute, followed by 46° C. for two minutes, then 72° C. for three minutes), in a total volume of 100 ul, which contained 10 ul of 10x concentrated Dynazyme buffer, 0.2 mM of each dNTP, 50 pmoles of each primer, and 2.5 units of Dynazyme DNA polymerase.

The probe was then purified via electrophoresis in low temperature melting agarose, as described by Sambrook et al., supra. Following purification, the probe was radiolabelled with α$^{32}$P, using a commercially available, random priming kit (radioactive nucleotide was α$^{32}$P dCTP).

Once the probes were labelled, they were used in a hybridization buffer (10% sodium salt of dextran sulfate, MW 500,000; 1% SDS; 1 M NaCl, and 50 ug/ml of denatured salmon sperm DNA). About 150 ng of $^{32}$P labelled probe (approximately $1.6 \times 10^8$ cpm), were put into a total volume of 200 ml of this buffer. Approximately 500,000 immobilized plaques on filters were hybridized filter which was combined with the nylon membrane containing at 65° C. for about 15 hours. The membranes were then washed with 0.2×SSC, 0.1% SDS, at 65° C.

Following autoradiography, one positive clone was found. When excised, the insert was found to be about 11 kilobases long. Three fragments (175 base pairs, 4.5 kilobases, and 6.5 kilobases) resulted from treatment of the insert with the endonuclease SstI, and these were then subcloned into the plasmids pBluescript SK(−), and pTZ19R, both of which are commercially available. The fragments were sequenced in their entirety, using commercially available enzymes, and primers 5'-labelled with $[\gamma^{33}P]ATP$. The sequence of the genomic clone is provided as SEQ ID NO: 29.

The foregoing examples show the isolation of nucleic acid molecules which code for tumor rejection antigen precursors and tumor rejection antigens. These molecules, however, are not homologous with any of the previously disclosed MAGE and BAGE coding sequences described in the reference set forth supra. Hence, one aspect of the invention is an isolated nucleic acid molecule which comprises the nucleotide sequence set forth in SEQ ID NO: 1 as well as fragments thereof, such as nucleotides 1–170, and 51–170, and any other fragment which is processed to a tumor rejection antigen. The sequence of SEQ ID NO: 1 is neither a MAGE nor a BAGE coding sequence, as will be seen by comparing it to the sequence of any of these genes as described in the cited references. Also a part of the invention are those nucleic acid molecules which also code for a non-MAGE and non-BAGE tumor rejection antigen precursor but which hybridize to a nucleic acid molecule containing the described nucleotide sequence, under stringent conditions. The term "stringent conditions" as used herein refers to parameters with which the art is familiar. More specifically stringent conditions, as used herein, refers to hybridization in 1 M NaCl, 1% SDS, and 10% dextran sulfate. This is followed by two washes of the filter at room temperature for 5 minutes, in 2×SSC, and one wash for 30 minutes in 2×SSC, 0.1% SDS. There are other conditions, reagents, and so forth which can be used, which result in the same or higher degree of stringency. The skilled artisan will be familiar with such conditions, and, thus, they are not given here.

It will also be seen from the examples that the invention embraces the use of the sequences in expression vectors, as well as to transform or transfect host cells and cell lines, be these prokaryotic (e.g., E. coli), or eukaryotic (e.g., CHO or COS cells). The expression vectors require that the pertinent sequence, i.e., those described supra, be operably linked to a promoter, As it has been found that human leukocyte antigen HLA-Cw6 presents a tumor rejection antigen derived from these genes, the expression vector may also include a nucleic acid molecule coding for HLA-Cw6. In a situation where the vector contains both coding sequences, it can be used to transfect a cell which does not normally express either one. The tumor rejection antigen precursor coding sequence may be used alone, when, e.g., the host cell already expresses HLA-Cw6. Of course, there is no limit on the particular host cell which can be used. As the vectors which contain the two coding sequences may be used in HLA-Cw6 presenting cells if desired, and the gene for tumor rejection antigen precursor can be used in host cells which do not express HLA-Cw6.

The invention also embraces so called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

To distinguish the nucleic acid molecules and the TRAPs of the invention from the previously described MAGE and BAGE materials, the invention shall be referred to as the GAGE family of genes and TRAPs. Hence, whenever "GAGE" is used herein, it refers to the tumor rejection antigen precursors coded for by the previously described sequences. "GAGE coding molecule" and similar terms, are used to describe the nucleic acid molecules themselves.

The invention as described herein has a number of uses, some of which are described herein. First, the invention permits the artisan to diagnose a disorder such as melanoma, characterized by expression of the TRAP, or presentation of the tumor rejection antigen. These methods involve determining expression of the TRAP gene, and/or TRAs derived therefrom, such as a TRA presented by HLA-Cw6. In the former situation, such determinations can be carried out via any standard nucleic acid determination assay, including the polymerase chain reaction, or assaying with labelled hybridization probes. In the latter situation, assaying with binding partners for complexes of TRA and HLA, such as antibodies, is especially preferred. An alternate method for determination is a TNF release assay, of the type described supra. To carry out the assay, it is preferred to make sure that testis cells are not present, as these normally express GAGE. This is not essential, however, as one can routinely differentiate between testis and other cell types. Also, it is practically impossible to have testis cells presents in non-testicular sample.

The isolation of the TRAP gene also makes it possible to isolate the TRAP molecule itself, especially TRAP molecules containing the amino acid sequence codes for by SEQ ID NOS: 2–6. These isolated molecules when presented as the TRA, or as complexes of TRA and HLA, such as HLA-Cw6 or HLA-A29 may be combined with materials such as adjuvants to produce vaccines useful in treating disorders characterized by expression of the TRAP molecule.

Exemplary adjuvants include Freund's complete and incomplete adjuvant, killed B. pertussis organism, "BCG", or Bacille Calmente-Guerin, Al(OH)$_3$, muramyl dipeptide and its derivatives which may be emulsified in metabolizable oils, such as squalene, monophosphoryl lipid A (MPL), keyhold limpet hemocyanin (KLH), saponin extracts such as QA-7, AQ-19, and QA-21 (also referred to as QS-21), these having been described in U.S. Pat. No. 5,057,540 to Kensil et al., incorporated by reference, MTP-MF59, N-[1-(2,3-dioleoyloxy)propyl]-N,N,N-trimethylammonium methyl sulfate (DOTAP), the cationic amphiphile DOTMA, the neutral phospholipids such as DOPE, and combinations of these. This listing is by no means comprehensive, and the artisan of ordinary skill will be able to augment this listing. All additional adjuvants are encompassed herein.

In addition, vaccines can be prepared from cells which present the TRA/HLA complexes on their surface, such as non-proliferative cancer cells, non-proliferative transfectants, etcetera. In all cases where cells are used as a vaccine, these can be cells transfected with coding sequences for one or both of the components necessary to provide a CTL response, or be cells which express both molecules without transfection. Further, the TRAP molecule, its associated TRAs, as well as complexes of TRA and HLA, may be used to produce antibodies, using standard techniques well known to the art.

When "disorder" is used herein, it refers to any pathological conditions where the tumor rejection antigen precursor is expressed. An example of such a disorder is cancer, melanoma in particular. Melanoma is well known as a cancer of pigment producing cells.

As indicated, supra, tumor rejection antigens, such as the one presented in SEQ ID NO: 4 are also a part of the invention. Also a part of the invention are polypeptides, such as molecules containing from 8 to 16 amino acids, where the polypeptides contain the amino acid sequence set forth in SEQ ID NO: 4. As the examples indicate, those peptides which are longer than the octamer of SEQ ID NO: 4 are processed into the tumor rejection anitgen of SEQ ID NO: 4 by the HLA-Cw6 presenting cancer cells, and presented thereby. The presentation leads to lysis by cytolytic T lymphocytes present in a body fluid sample contacted to the cells presenting the complex. Similarly, the peptides longer than SEQ ID NO: 22, such as SEQ ID NO: 21, are processed to the appropriate TRA, and are presented by cancer cells, such as HLA-A29 positive cells.

Thus, another feature of the invention are peptides which are anywhere from 9 to 16 amino acids long, and comprise the sequence:

Xaa Xaa Trp Xaa Xaa Xaa Xaa Xaa Trp (SEQ ID NO: 23)
where Xaa is any amino acid. These peptides bend to, and/or are processed to peptides which bind to HLA-A29 molecules. The fact that these peptides are processed to the tumor rejection antigen, is indicated by the examples.

This property may be exploited in the context of other parameters in confirming diagnosis of pathological conditions, such as cancer, melanoma in particular. For example, the investigator may study antigens shed into blood or urine, observe physiological changes, and then confirm a diagnosis of melanoma using the CTL proliferation methodologies described herein.

On their own, peptides in accordance with the invention may be used to carry out HLA-typing assays. It is well known that when a skin graft, organ transplant, etc., is necessary one must perform HLA typing so as to minimize the possibility of graft rejection. The peptides of the invention may be used to determine whether or not an individual is HLA-Cw6 positive, so that appropriate donors may be selected. This type of assay is simple to carry out. The peptides of the invention are contacted to a sample of interest, and binding to cells in that sample indicates whether or not the individual from which the sample is taken is HLA-Cw6 positive. One may label the peptides themselves, conjugate or otherwise bind them to linkers which are labeled, immobilize them to solid phases, and so forth, so as to optimize such an assay. Other standard methodologies will be clear to the skilled artisan, and need not be presented herein.

Therapeutic approaches based upon the disclosure are premised on a response by a subject's immune system, leading to lysis of TRA presenting cells, such as HLA-Cw6 cells. One such approach is the administration of CTLs specific to the complex to a subject with abnormal cells of the phenotype at issue. It is within the skill of the artisan to develop such CTLs in vitro. Specifically, a sample of cells, such as blood cells, are contacted to a cell presenting the complex and capable of provoking a specific CTL to proliferate. The target cell can be a transfectant, such as a COS cell of the type described supra. These transfectants present the desired complex on their surface and, when combined with a CTL of interest, stimulate its proliferation. COS cells, such as those used herein are widely available, as are other suitable host cells.

To detail the therapeutic methodology, referred to as adoptive transfer (Greenberg, J. Immunol. 136(5): 1917 (1986); Riddel et al., Science 257:238 (7-10-92); Lynch et al., Eur. J. Immunol. 21: 1403–1410 (1991); Kast et al., Cell 59: 603–614 (11-17-89), cells presenting the desired complex are combined with CTLs leading to proliferation of the CTLs specific thereto. The proliferated CTLs are then administered to a subject with a cellular abnormality which is characterized by certain of the abnormal cells presenting the particular complex, where the complex contains the pertinent HLA molecule. The CTLs then lyse the abnormal cells, thereby achieving the desired therapeutic goal.

The foregoing therapy assumes that at least some of the subject's abnormal cells present the relevant HLA/TRA complex. This can be determined very easily, as the art is very familiar with methods for identifying cells which present a particular HLA molecule, as well as how to identify cells expressing RNA of the pertinent sequences, in this case a GAGE sequence. Once cells presenting the relevant complex are identified via the foregoing screening methodology, they can be combined with a sample from a patient, where the sample contains CTLs. If the complex presenting cells are lysed by the mixed CTL sample, then it can be assumed that a GAGE derived, tumor rejection antigen is being presented, and the subject is an appropriate candidate for the therapeutic approaches set forth supra.

Adoptive transfer is not the only form of therapy that is available in accordance with the invention. CTLs can also be provoked in vivo, using a number of approaches. One approach, i.e., the use of non-proliferative cells expressing the complex, has been elaborated upon supra. The cells used in this approach may be those that normally express the complex, such as irradiated melanoma cells or cells transfected with one or both of the genes necessary for presentation of the complex. Chen et al., Proc. Natl. Acad. Sci. USA 88: 110–114 (January, 1991) exemplifies this approach, showing the use of transfected cells expressing HPV E7 peptides in a therapeutic regime. Various cell types may be used. Similarly, vectors carrying one or both of the genes of interest may be used. Viral or bacterial vectors are especially preferred. In these systems, the gene of interest is carried by, e.g., a Vaccinia virus or the bacteria BCG, and the materials de facto "infect" host cells. The cells which result present the complex of interest, and are recognized by autologous CTLs, which then proliferate. A similar effect can be achieved by combining the tumor rejection antigen or the precursor itself with an adjuvant to facilitate incorporation into HLA-Cw6 presenting cells which then present the HLA/peptide complex of interest. The TRAP is processed to yield the peptide partner of the HLA molecule while the TRA is presented without the need for further processing.

Other aspects of the invention will be clear to the skilled artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An isolated nucleic acid molecule consisting of a nucleotide sequence, the complementary sequence of which hybridizes under stringent conditions to SEQ ID NO: 29, wherein said isolated nucleic acid molecule encodes a GAGE tumor rejection antigen precursor.

2. The isolated nucleic acid molecule of claim 1, which encodes a protein the amino acid sequence of which is the amino acid sequence encoded by SEQ ID NO: 29.

3. The isolated nucleic acid molecule of claim 1, wherein said nucleic acid molecule is genomic DNA.

4. An isolated nucleic acid molecule which consists of:
   (a) nucleotides 1–119 of SEQ ID NO: 1;
   (b) nucleotides 1–170 of SEQ ID NO: 1;
   (c) nucleotides 20–328 of SEQ ID NO: 1;
   (d) nucleotides 51–119 of SEQ ID NO: 1; or
   (e) nucleotides 51–170 of SEQ ID NO: 1.

5. An isolated nucleic acid molecule consisting of at least nucleotides 18–34 of SEQ ID NO: 1 and no more than nucleotides 18–326 of SEQ ID NO: 1.

6. An isolated nucleic acid molecule which encodes a peptide whose amino acid sequence consists of SEQ ID NO: 4, 5, 6, 7, 8, 12 or 13.

7. The isolated nucleic acid molecule of claim 1, consisting of SEQ ID NO: 29.

8. Expression vector comprising the isolated nucleic acid molecule of claim 2, operably linked to a promotor.

9. Expression vector comprising the isolated nucleic acid molecule of claim 7, operably linked to a promotor.

10. Isolated eukaryotic cell transformed or transfected with the expression vector of claim 8.

11. Isolated eukaryotic cell transformed or transfected with the expression vector of claim 9.

12. Process for making an expression vector capable of encoding a GAGE tumor rejection antigen precursor, comprising inserting the isolated nucleic acid molecule of claim 2, into a vector which comprises a promoter, wherein said isolated nucleic acid molecule is inserted into said expression vector in operable linkage orientation to said promoter.

13. Process for making an expression vector capable of encoding a GAGE tumor rejection antigen precursor, comprising inserting the isolated nucleic acid molecule of claim 7 into a vector which comprises a promoter, wherein said isolated nucleic acid molecule is inserted into said expression vector in operable linkage orientation to said promotor.

14. A process for determining expression of a GAGE tumor rejection antigen precursor, comprising contacting a sample containing a nucleic acid molecule with an isolated nucleic acid molecule which hybridizes under stringent conditions with the nucleotide sequence of SEQ ID NO: 29, and determining hybridization of said isolated nucleic acid molecule in said sample to a nucleic acid molecule as a determination of expression of a GAGE tumor rejection antigen precursor.

* * * * *

UNITED STATES PATENT AND TRADEMARK OFFICE
CERTIFICATE OF CORRECTION

PATENT NO. : 6,013,481
DATED : January 11, 2000
INVENTOR(S) : DeBacker et al.

Page 1 of 1

It is certified that error appears in the above-identified patent and that said Letters Patent is hereby corrected as shown below:

Column 2,
Line 56, change "do no show" to read as -- do not show --.
Line 62, change "longs" to read as -- long --.

Column 3,
Line 32, change "MZ22MEL.43" to read as -- MZ2-MEL.43 --.

Column 6,
Line 2, change "F" to read as -- F --.
Line 13, change "2N6" to read as -- 2D6 --.
Line 62, change "are" to read as -- art --.
Line 67, insert a comma after the word "Next" to read as -- Next, --.

Column 7,
Line 37, change "testes" to read as -- testis --.

Column 9,
Line 29, change "NO: 3" to read as -- NO: 13 --.
Line 30, change "NO: 2" to read as -- NO: 12 --.
Line 35, change "NO: 3" to read as -- NO: 13 --.

Column 16,
Line 50, change "AQ-19" to read as -- QA-19 --.

Signed and Sealed this

Twentieth Day of November, 2001

Attest:

NICHOLAS P. GODICI
Attesting Officer    Acting Director of the United States Patent and Trademark Office